US009056892B2

United States Patent

(12) United States Patent
Pun et al.

(10) Patent No.: US 9,056,892 B2
(45) Date of Patent: Jun. 16, 2015

(54) RETROGRADE TRANSPORT PEPTIDE AND USE OF SAME FOR DELIVERY TO CENTRAL NERVOUS SYSTEM

(75) Inventors: Suzie H. Pun, Seattle, WA (US); Drew L. Sellers, Seattle, WA (US); Jamie M. Bergen, Mountain View, CA (US); Philip J. Horner, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 0 days.

(21) Appl. No.: 14/238,724

(22) PCT Filed: Sep. 8, 2012

(86) PCT No.: PCT/US2012/054334
§ 371 (c)(1),
(2), (4) Date: Feb. 12, 2014

(87) PCT Pub. No.: WO2013/036889
PCT Pub. Date: Mar. 14, 2013

(65) Prior Publication Data

US 2014/0178381 A1 Jun. 26, 2014

Related U.S. Application Data

(60) Provisional application No. 61/532,982, filed on Sep. 9, 2011.

(51) Int. Cl.

| | |
|---|---|
| ***C07K 7/08*** | (2006.01) |
| ***C07K 7/06*** | (2006.01) |
| ***C12N 9/00*** | (2006.01) |
| ***A61K 38/08*** | (2006.01) |
| ***A61K 38/10*** | (2006.01) |

(52) U.S. Cl.
CPC ... *C07K 7/08* (2013.01); *C07K 7/06* (2013.01); *C12N 9/00* (2013.01); *C07K 2319/00* (2013.01); *C07K 2319/21* (2013.01); *A61K 38/08* (2013.01); *A61K 38/10* (2013.01)

(58) Field of Classification Search
CPC ........ C07K 7/06; C07K 7/08; C07K 2319/00; C07K 2319/21; A61K 38/08; A61K 38/10; C12N 9/00
See application file for complete search history.

(56) References Cited

U.S. PATENT DOCUMENTS

| | | | | |
|---|---|---|---|---|
| 2005/0136051 | A1* | 6/2005 | Scallon | 424/133.1 |
| 2006/0048240 | A1* | 3/2006 | Alexandrov et al. | 800/278 |
| 2007/0044171 | A1* | 2/2007 | Kovalic et al. | 800/278 |

FOREIGN PATENT DOCUMENTS

| | | |
|---|---|---|
| WO | 2009006638 A2 | 1/2009 |

OTHER PUBLICATIONS

Zhang et al., 2002, Regulated Nuclear Trafficking of the Homeodomain Protein Otx1 in Cortical Neurons, Molecular and Cellular Neuroscience, 19: 430-446.*

Alvarez-Erviti, L., et al., Delivery of siRNA to the mouse brain by systemic injection of targeted exosomes. Nature Biotechnology, 2011. 29(4): p. 341-U179.

Azzouz, M., et al., VEGF delivery with retrogradely transported lentivector prolongs survival in a mouse ALS model. Nature, 2004. 429(6990): p. 413-417.

Boulis, N.M., et al., Characterization of adenoviral gene expression in spinal cord after remote vector delivery. Neurosurgery, 1999. 45(1): p. 131-137.

Bray, B.L., Large-scale manufacture of peptide therapeutics by chemical synthesis. Nature Reviews Drug Discovery, 2003. 2(7): p. 587-593.

Carlton, E., et al., Fusion of the Tetanus Toxin C Fragment Binding Domain and BCL-XL for Protection of Peripheral Nerve Neurons. Neurosurgery, 2008. 63(6): p. 1175-1182.

Chian, R.J., et al., IGF-1:Tetanus toxin fragment C fusion protein improves delivery of IGF-1 to spinal cord but fails to prolong survival of ALS mice. Brain Research, 2009. 1287: p. 1-19.

Federici, T. and N.M. Boulis, Gene-based treatment of motor neuron diseases. Muscle & Nerve, 2006. 33(3): p. 302-323.

Federici, T., et al., A means for targeting therapeutics to peripheral nervous system neurons with axonal damage. Neurosurgery, 2007. 60(5): p. 911-918.

Figueiredo, D.M., et al., Delivery of recombinant tetanus-superoxide dismutase proteins to central nervous system neurons by retrograde axonal transport. Experimental Neurology, 1997. 145(2): p. 546-554.

Figueiredo, D.M., et al., Interaction of tetanus toxin derived hybrid proteins with neuronal cells. Journal of Natural Toxins, 2000. 9(4): p. 363-379.

Foust, K.D., et al., Rescue of the spinal muscular atrophy phenotype in a mouse model by early postnatal delivery of SMN. Nature Biotechnology, 2010. 28(3): p. 271-U126.

Glorioso, J.C. and D.J. Fink, Herpes Vector-mediated Gene Transfer in the Treatment of Chronic Pain. Molecular Therapy, 2009. 17(1): p. 13-18.

Kaspar, B.K., et al., Retrograde viral delivery of IGF-1 prolongs survival in a mouse ALS model. Science, 2003. 301(5634): p. 839-842.

Li, J.H., et al., Insect GDNF:TTC fusion protein improves delivery of GDNF to mouse CNS. Biochemical and Biophysical Research Communications, 2009. 390(3): p. 947-951.

Mitchell, J.D. and G.D. Borasio, Amyotrophic lateral sclerosis. Lancet, 2007. 369(9578): p. 2031-2041.

Monani, U.R., Spinal muscular atrophy: A deficiency in a ubiquitous protein; a motor neuron-specific disease. Neuron, 2005. 48(6): p. 885-896.

(Continued)

*Primary Examiner* — Amber D Steele
(74) *Attorney, Agent, or Firm* — Karen S. Canady; canady + lortz LLP

(57) ABSTRACT

Transport peptides, alone or attached to a cargo moiety, are capable of targeted axonal import into the spinal cord and other structures of the central nervous system. The transport peptides can be used to deliver therapeutic agents and other molecules of interest from the periphery to the central nervous system, providing a means to detect, treat or prevent neurodegenerative diseases, stroke, chronic pain and other conditions via minimally invasive techniques of administration.

20 Claims, 8 Drawing Sheets

(56) References Cited

OTHER PUBLICATIONS

Montet, X., et al., Multivalent effects of RGD peptides obtained by nanoparticle display. Journal of Medicinal Chemistry, 2006. 49(20): p. 6087-6093.

Pasqualini, R. and E. Ruoslahti, Organ targeting in vivo using phage display peptide libraries. Nature, 1996. 380(6572): p. 364-366.

Pasqualini, R., E. Koivunen, and E. Ruoslahti, alpha v Integrins as receptors for tumor targeting by circulating ligands. Nature Biotechnology, 1997. 15(6): p. 542-546.

Perez, M.C.P., et al., Comparative analysis of genomic HSV vectors for gene delivery to motor neurons following peripheral inoculation in vivo. Gene Therapy, 2004. 11(13): p. 1023-1032.

Scott, J.K. and G.P. Smith, Searching for Peptide Ligands With an Epitope Library. Science, 1990. 249(4967): p. 386-390.

Terskikh, A.V., et al., "Peptabody": A new type of high avidity binding protein. Proceedings of the National Academy of Sciences of the United States of America, 1997. 94(5): p. 1663-1668.

Vlieghe, P., et al., Synthetic therapeutic peptides: science and market. Drug Discovery Today, 2010. 15(1-2): p. 40-56.

Yu, Y.J., et al., Boosting Brain Uptake of a Therapeutic Antibody by Reducing Its Affinity for a Transcytosis Target. Science Translational Medicine, 2011. 3(84).

Kwon, Ester J., Targeted nonviral delivery vehicles to neural progenitor cells in the mouse subventricular zone, Biomaterials. Mar. 2010 ; 31(8): 2417. doi:10.1016/j.biomaterials.2009.11.086.

Park, In-Kyu, Neuron-specific delivery of nucleic acids mediated by Tet1-modified poly(ethylenimine), J Gene Med. Aug. 2007 ; 9(8): 691-702. doi:10.1002/jgm.1062.

Written Opinion of the International Searching Authority, and International Search Report related to corresponding PCT International application No. PCT/US2012/054334, 6 pages 2012.

* cited by examiner

SEQUENCE LISTING

<160> NUMBER OF SEQ ID NOS: 20

<210> SEQ ID NO 1
<211> LENGTH: 7
<212> TYPE: PRT
<213> ORGANISM: Artificial Sequence
<220> FEATURE:
<223> OTHER INFORMATION: synthetic peptide

<400> SEQUENCE: 1

Gln Ser Gln Ser Gln Met Arg
1               5

<210> SEQ ID NO 2
<211> LENGTH: 7
<212> TYPE: PRT
<213> ORGANISM: Artificial Sequence
<220> FEATURE:
<223> OTHER INFORMATION: synthetic peptide

<400> SEQUENCE: 2

Ala Ser Gly Ala Gln Ala Arg
1               5

<210> SEQ ID NO 3
<211> LENGTH: 4
<212> TYPE: PRT
<213> ORGANISM: Artificial Sequence
<220> FEATURE:
<223> OTHER INFORMATION: synthetic peptide

<400> SEQUENCE: 3

Cys Pro Phe Cys
1

<210> SEQ ID NO 4
<211> LENGTH: 7
<212> TYPE: PRT
<213> ORGANISM: Artificial Sequence
<220> FEATURE:
<223> OTHER INFORMATION: synthetic peptide

<400> SEQUENCE: 4

Leu Gln Ala Thr Pro Ser Ala
1               5

<210> SEQ ID NO 5
<211> LENGTH: 7
<212> TYPE: PRT
<213> ORGANISM: Artificial Sequence
<220> FEATURE:
<223> OTHER INFORMATION: synthetic peptide

<400> SEQUENCE: 5

Ile Ser Pro Ser Leu Ser Ser
1               5

<210> SEQ ID NO 6
<211> LENGTH: 7
<212> TYPE: PRT
<213> ORGANISM: Artificial Sequence
<220> FEATURE:
<223> OTHER INFORMATION: synthetic peptide

<400> SEQUENCE: 6

Thr Ser Thr Gly Phe Arg Gly
1               5

-continued

```
<210> SEQ ID NO 7
<211> LENGTH: 14
<212> TYPE: PRT
<213> ORGANISM: Artificial Sequence
<220> FEATURE:
<223> OTHER INFORMATION: synthetic peptide

<400> SEQUENCE: 7

Thr Ser Thr Ala Pro His Leu Arg Leu Arg Leu Thr Ser Arg
1               5                   10


<210> SEQ ID NO 8
<211> LENGTH: 14
<212> TYPE: PRT
<213> ORGANISM: Artificial Sequence
<220> FEATURE:
<223> OTHER INFORMATION: synthetic peptide

<400> SEQUENCE: 8

Ser Ala Cys Gln Ser Gln Ser Gln Met Arg Cys Gly Gly Gly
1               5                   10


<210> SEQ ID NO 9
<211> LENGTH: 13
<212> TYPE: PRT
<213> ORGANISM: Artificial Sequence
<220> FEATURE:
<223> OTHER INFORMATION: synthetic peptide

<400> SEQUENCE: 9

Gly Gly Cys Ala Ser Gly Ala Gln Ala Arg Cys Gly Gly
1               5                   10


<210> SEQ ID NO 10
<211> LENGTH: 9
<212> TYPE: PRT
<213> ORGANISM: Artificial Sequence
<220> FEATURE:
<223> OTHER INFORMATION: synthetic peptide

<400> SEQUENCE: 10

Ser Ala Cys Pro Phe Cys Gly Gly Gly
1               5


<210> SEQ ID NO 11
<211> LENGTH: 14
<212> TYPE: PRT
<213> ORGANISM: Artificial Sequence
<220> FEATURE:
<223> OTHER INFORMATION: synthetic peptide

<400> SEQUENCE: 11

Ser Ala Cys Leu Gln Ala Thr Pro Ser Ala Cys Gly Gly Gly
1               5                   10


<210> SEQ ID NO 12
<211> LENGTH: 14
<212> TYPE: PRT
<213> ORGANISM: Artificial Sequence
<220> FEATURE:
<223> OTHER INFORMATION: synthetic peptide

<400> SEQUENCE: 12

Ser Ala Cys Ile Ser Pro Ser Leu Ser Ser Cys Gly Gly Gly
1               5                   10
```

<210> SEQ ID NO 13
<211> LENGTH: 14
<212> TYPE: PRT
<213> ORGANISM: Artificial Sequence
<220> FEATURE:
<223> OTHER INFORMATION: synthetic peptide

<400> SEQUENCE: 13

Ser Ala Cys Thr Ser Thr Gly Phe Arg Gly Cys Gly Gly Gly
1               5                   10

<210> SEQ ID NO 14
<211> LENGTH: 7
<212> TYPE: PRT
<213> ORGANISM: Artificial Sequence
<220> FEATURE:
<223> OTHER INFORMATION: synthetic peptide

<400> SEQUENCE: 14

Pro Pro Lys Lys Arg Lys Val
1               5

<210> SEQ ID NO 15
<211> LENGTH: 6
<212> TYPE: PRT
<213> ORGANISM: Artificial Sequence
<220> FEATURE:
<223> OTHER INFORMATION: synthetic peptide

<400> SEQUENCE: 15

Pro Lys Lys Arg Lys Val
1               5

<210> SEQ ID NO 16
<211> LENGTH: 42
<212> TYPE: DNA
<213> ORGANISM: Artificial Sequence
<220> FEATURE:
<223> OTHER INFORMATION: synthetic construct

<400> SEQUENCE: 16
tctgcttgtc agtctcagtc tcagatgcgg tgcggtggag gt 42

<210> SEQ ID NO 17
<211> LENGTH: 39
<212> TYPE: DNA
<213> ORGANISM: Artificial Sequence
<220> FEATURE:
<223> OTHER INFORMATION: synthetic construct

<400> SEQUENCE: 17
ggtggttgtg cttctggtgc tcaagctcgt tgtggtggt 39

<210> SEQ ID NO 18
<211> LENGTH: 27
<212> TYPE: DNA
<213> ORGANISM: Artificial Sequence
<220> FEATURE:
<223> OTHER INFORMATION: synthetic construct

<400> SEQUENCE: 18
tctgcttgtc ctttttgtgg tggtggt 27

<210> SEQ ID NO 19
<211> LENGTH: 42
<212> TYPE: DNA

-continued

```
<213> ORGANISM: Artificial Sequence
<220> FEATURE:
<223> OTHER INFORMATION: synthetic construct

<400> SEQUENCE: 19

acctccaccg caccgcatct gagactgaga ctgacaagca ga                    42


<210> SEQ ID NO 20
<211> LENGTH: 14
<212> TYPE: PRT
<213> ORGANISM: Artificial Sequence
<220> FEATURE:
<223> OTHER INFORMATION: synthetic peptide

<400> SEQUENCE: 20

Ser Ala Ala Gln Ser Gln Ser Gln Met Arg Ala Gly Gly Gly
1               5                   10
```

RETROGRADE TRANSPORT PEPTIDE AND USE OF SAME FOR DELIVERY TO CENTRAL NERVOUS SYSTEM

This application is the National Stage of International Application No. PCT/US2012/054334, filed Sep. 8, 2012, which application claims the benefit of U.S. provisional patent application No. 61/532,982, filed Sep. 9, 2011, the entire contents of which are incorporated herein by reference.

STATEMENT REGARDING FEDERALLY SPONSORED RESEARCH

This invention was made with government support under BES 0454324 awarded by the National Science Foundation and R01 NS064404 awarded by the National Institutes of Health. The government has certain rights in the invention.

TECHNICAL FIELD OF THE INVENTION

The present invention relates to molecules and methods for transport of molecules from to the central nervous system (CNS). More specifically, the invention relates to transport peptides, alone or attached to a cargo moiety, that can be administered peripherally for CNS delivery. The transport peptides can be used to deliver therapeutic agents, imaging agents and other molecules of interest to the central nervous system, providing a means to detect, treat or prevent neurodegenerative diseases, stroke, chronic pain and other conditions.

BACKGROUND OF THE INVENTION

Therapeutics designed to treat neurodegenerative diseases that affect motor and sensory neurons, such as amyotrophic lateral sclerosis (ALS), spinal muscular atrophy (SMA) or chronic pain, have had limited efficacy due to the formidable challenges associated with delivery to the central nervous system (CNS). The inability to cross the blood-spinal cord and blood-brain barrier (BBB) after systemic delivery and insufficient penetration into the parenchyma from the cerebrospinal fluid (CSF) has hampered the use of recombinant neurotrophic factors and proteins. Substantial advances have been recently reported for brain-specific delivery of transcytosing peptide or antibody carriers and brain-targeted exosomes that show promise toward the treatment of brain-afflicting diseases like Alzheimer's disease. Still, few therapeutic options are available for degenerative diseases that affect motor neurons in the spinal cord and of the drugs that have been identified many have been biologics such as proteins, genes and small interfering RNAs that are not readily transported into the nervous system.

Therapeutic molecules can be delivered to the spinal cord by direct injection, remote delivery or intrathecal transplantation of genetically modified cells secreting the molecules of interest. Several engineered viruses that are capable of transducing motor neurons have been used to demonstrate the potential of remote gene transfer in animal models of disease, and ligands for the tetanus toxin receptor have been fused to proteins for delivery to spinal cord neurons, although in general functional protein delivery has not been observed using this strategy.

There remains a need for peptides and related molecules that mediate delivery into the CNS via retrograde transport.

SUMMARY OF THE INVENTION

The invention provides a recombinant or synthetic transport peptide, or polynucleotide encoding same, and methods of using the transport peptide to deliver molecules to the central nervous system. In a typical embodiment, the peptide has the amino acid sequence QSQSQMR (SEQ ID NO: 1), ASGAQAR (SEQ ID NO: 2), PF (amino acids 2-3 of SEQ ID NO: 3) or TSTAPHLRLRLTSR (SEQ ID NO: 7). Optionally, the transport peptide further comprises a flanking sequence that mediates incorporation into a carrier. In one embodiment, the peptide is flanked with a cysteine residue on either side of the core transport peptide. In some embodiments, the peptide further comprises a heterologous molecule attached thereto. Representative examples of the heterologous molecule include, but are not limited to, a polypeptide, antibody, polynucleotide, imaging contrast agent, vector, delivery vehicle, small molecule, drug and or an attachment domain. In a typical embodiment, the polypeptide is an enzyme or a growth factor. Representative examples of polypeptides for use with the invention include, but are not limited to, survival motor neuron (SMN) protein, glial-derived neurotrophic factor (GDNF), brain-derived neurotrophic factor (BDNF), fibroblast growth factor (FGF), vascular endothelial growth factor (VEGF), nerve growth factor (NGF), neurotrophin (NT), transforming growth factor (TGF), ciliary neurotrophic factor (CNTF), epidermal growth factor (EGF), insulin-like growth factor (IGF), stromal cell factor (SCF), notch, heparan sulfate proteoglycans (HSPGs) and growth factors within these classes such as, for example, NT-3, NT-4/5, NT-6, IGF-1, IGF-2, bFGF, neurturin, persephin, artemin, TGFα, TGFβ, PDGF, FGF-2, SCF-1 and BMP, FGF20, VIP, and pleiotrophin (PTN).

In addition to the above examples of polypeptides as heterologous molecules for delivery via a transport peptide of the invention, antibodies and functional fragments thereof are contemplated. Conventional antibodies and fragments thereof, as well as intrabodies (IAbs), can be used in a therapeutic context. For example, a transport peptide of the invention can be used to deliver one or more antibodies to slow or halt disease progression. Antibodies targeting tau and/or beta-amyloid protein (bap), for example, can be used to slow progression of Alzheimer's disease. Antibodies targeting α-synuclein, as another example, can be used to treat Parkinson's disease. The onset or progression of Huntington's disease may be delayed by treatment with antibodies targeting mutant Huntingtin protein. Intrabodies, (labs), are intracellularly expressed antibody fragments consisting only of antigen recognition domain(s), that can be designed to recognize either distinct conformations or distinct epitopes in proteins that cause neurodegenerative diseases. Examples of epitope-specific intrabody therapies being developed for treatment of Alzheimer's disease, Huntington's disease and Parkinson's disease are described in Southwell and Patterson, 2010, *Reviews in the Neurosciences* 21, 273-287.

Representative polynucleotides suitable for use with the invention include, but are not limited to, antisense polynucleotides, such as ribozymes and small interfering RNA (siRNA) molecules as well as other RNA-based therapeutics (see, e.g., Kole et al., 2012, Nat Rev Drug Discov., 11(2):125-40). Some examples of siRNAs that can be used to treat neurodegenerative diseases include those which target the mRNA for the α-synuclein protein, the mRNA for BACE1 (including variants thereof, e.g. variants A, B, C, and D), the mRNA for huntingtin protein, the mRNA for ataxin1 protein, the mRNA for ataxin3 protein, or the mRNA for atrophin-1 protein.

The heterologous molecule can be attached to the transport peptide using any of a variety of conventional techniques known to those skilled in the art, such as by chemical conjugation, non-covalent affinity interactions, electrostatic interaction, or expression as a fusion partner. In one embodiment, the transport peptide is a fusion protein comprising the transport peptide fused with a heterologous peptide or protein. Examples of heterologous peptides or proteins include, but are not limited to, enzymes, growth factors, antibodies, agonist or antagonist ligands, and therapeutic peptides.

The methods of the invention make use of the transport peptide for retrograde transport from a peripheral site to the central nervous system (CNS). In one embodiment, the invention provides a method of delivering a molecule to a CNS site of a subject. In another embodiment, the invention provides a method of treating a CNS condition in a subject. The method comprises administering the transport peptide, to which a heterologous molecule is attached, to a peripheral site of the subject. The transport peptide and the heterologous molecule are then transported from the peripheral site to the spinal cord. In some embodiments, the transport peptide and its cargo are delivered trans-synaptically to interneurons, sensory neurons, and to higher CNS structures. The CNS site for delivery by the method is thus the spinal cord, ventral horn motor neurons, DRG, brain, motor cortex, sensory cortex, basal ganglia, and other structures of the forebrain (including the cerebrum, thalamus and hypothalamus) and basal forebrain, midbrain (including the tectum and tegmentum), or hindbrain (including the pons, cerebellum, and medulla oblongata).

In a typical embodiment, the administering comprises intramuscular injection or implantation, intraperitoneal injection or implantation, intrathecal or epidural administration, intranasal administration, intravenous administration or subcutaneous injection. Oral or transdermal administration is contemplated, provided the transport peptide and its cargo are sufficiently protected from enzymatic degradation. Typically, the molecule delivered is a therapeutic agent. Examples of therapeutic agents include small molecules, polypeptides, antibodies, polynucleotides, and drugs. The CNS condition to be treated can be a neurodegenerative disease, stroke, or chronic pain. Additional examples of diseases or conditions to be treated include, but are not limited to, spinal muscular atrophy, Parkinson's disease, Alzheimer's disease, amyotrophic lateral sclerosis (ALS), progressive muscular atrophy (PMA), progressive bulbar palsy (PBP), primary lateral sclerosis (PLS), Creutzfeldt-Jakob disease, primary progressive aphasia, and progressive supranuclear palsy.

BRIEF DESCRIPTION OF THE FIGURES

FIG. 1A. Spinal Cord tissue from mice were harvested 8, 24, and 48 hours after intramuscular (IM) injection of M13 bacteriophage libraries ($1\times10^{10}$ pfu/μL). Recovered phage was then amplified and injected IM for three rounds of selection. FIG. 1B. Spinal cords divided into lower (lumbar-sacral) and upper (cervical-thoracic) regions showed a significant accumulation of clone-2404 phage particles compared against a circular-control phage.

FIG. 2A. Tissue sections of the lumbar spinal cord immunostained for Map2 (upper portions of insets), Bacteriophage M13 protein (middle portions of insets), GFAP (lower portions of insets) revealed distinctly different M13-staining in control versus 2404 phage-injected animals. In control phage-injected animals, confocal microscopy revealed M13 protein around vessel lumens (inset; arrow) with diffuse bacteriophage staining around vascular-lumens (*) in the cord parenchyma. In 2404-injected animals, M13 stain was seen by confocal microscopy to co-localize with Map2 and GFAP process, particularly around the root entry zone (inset). Bactriophage-M13 was localized along filamentous structures that extend through the root entry zone. FIG. 2B. Tissue from control- and 2404-phage injected animals immunostained for choline acetyl transferase (ChAT), M13 (middle portions of inset), and neuronal marker NeuN showed control phage does not colocalize with neurons; 2404-bactriophage (M13) colocalize with NeuN in ChAT labeled motor neurons to demonstrate clone-2404 entered the spinal cord via motor neurons that project to the periphery (inset). Scale bar, 10 μm.

FIG. 3A. Photomicrographs showing results after streptavidin:peptide complexes (Streptavidin control, SA:TAxI, and SA:TAxI$^L$) were added (0.1 μM) to primary cerebellar cultures prior to fixation. FIG. 3B. Bar graph showing results after streptavidin binding was evaluated by fluorescence intensity in primary neuron cultures incubated 30 minutes at 37° C. with streptavidin, SA:TAxI, or SA:TAxI$^L$. Bar, 50 μm). The integrated density of the fluorescence intensity showed a significant increase in neuronal cultures treated with SA:TAxI versus SA:TAxI$^L$ and Avidin alone. (, $p<0.01$. #, $p=0.08$.) FIG. 3**C. Tissue from the CNS was subdivided to determine the concentration of NA in the forebrain (F. Brain), hindbrain (H. Brain), cervical-thoracic cord (T. Cord), and lumbar-sacral cord (L. Cord) and showed that NA:TAxI complexes showed significantly increased concentrations versus other NA:peptide complexes. (*, $p>0.05$. **, $p<0.01$.)

FIG. 4A. Photomicrographs showing spinal cord tissue immunostained for NeutrAvidin (upper portion of trios of insets), FluoroGold (FGold; middle portion of trios of insets), and NeuN (lower portion of trios of insets), which revealed the incidence of NeutraAvidin:peptide complex delivery into the spinal cord. NA:TAxI labeled numerous neurons labeled by FGold. FIG. 4B. Graphs depicting quantification of neurons labeled with NA FGold within serial sections (1-in-6) of the lumbar spinal cord (L2-L5), which revealed a greater number and broader distribution of NA:TAxI complexes in the spinal cord compared to NA:TAxI$^Q$ complexes.

FIG. 6A. Confocal micrographs of ventral root motor neurons stained immunofluorescently for NueN (prominent cytoplasmic stain) and ChAT (lighter cytoplasmic staining) and TAxI-Qdots (primarily visible in the nuclear region). FIG. 6B. High magnification images of the ventral horn stained by immunofluorescence. FIG. 6C. High magnification images of the dorsal grey matter stained by immunofluorescence. FIG. 6D. Spinal cord tissue pre-blocked with 10-fold excess of TAxI-peptide prior to immunofluorescence for NeuN and ChAT and TAxI-QDots.

DETAILED DESCRIPTION OF THE INVENTION

Figure 1A:
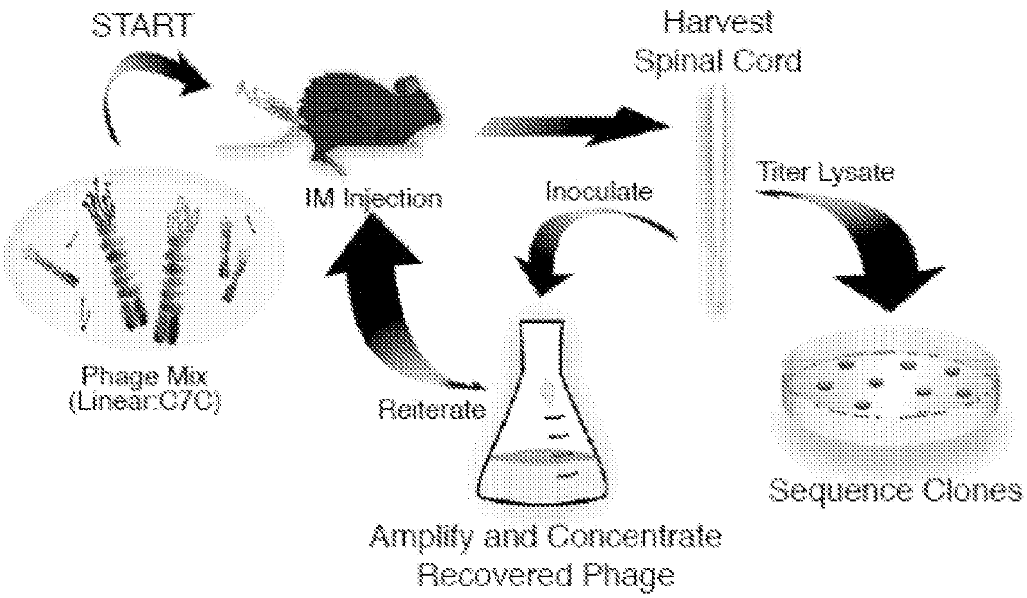
FIGS. 1A-1B. Illustrate the protocol for and results of in vivo screening for recombinant phage in the CNS after intramuscular injection.

The present invention is based on the discovery and identification of peptides that mediate delivery into the CNS via retrograde transport. The transport peptides described herein are trafficked into the spinal cord and target the processes and somas of motor neurons. One example of such a transport peptide, called TAxI (Targeted Axonal Import), has been demonstrated to deliver an active enzyme into the spinal cord neurons after peripheral muscle injection. The transport peptide can thus be used to convey imaging agents, transport therapeutic agents to treat a condition of the CNS, or to deliver regenerative agents in the case of nerve injury.

The transport peptides and methods of delivery disclosed herein overcome problems and limitations associated with preferential neuron delivery and endocytotic uptake and other methods previously attempted. For example, certain adeno-associated viruses (AAVs) must be delivered before the blood-brain and blood-cerebrospinal fluid barriers are fully formed, and some AAVs primarily transfect astrocytes in the CNS of adult mammals. Some viral delivery methods raise concerns regarding toxicity. Some delivery systems raise concerns of immunogenicity and/or are expensive to produce. Others successfully deliver cargo, but without retaining function. In contrast, a variety of cargo molecules have been tested using the present invention and found to be successfully transported to the CNS, without loss of biological activity, such as enzymatic function.

DEFINITIONS

All scientific and technical terms used in this application have meanings commonly used in the art unless otherwise specified. As used in this application, the following words or phrases have the meanings specified.

As used herein, "peptide" or "polypeptide" includes fragments of proteins, and peptides, whether isolated from natural sources, produced by recombinant techniques or chemically synthesized. Polypeptides (and peptides) of the invention typically comprise at least 2, more typically, at least about 6 amino acids. In some embodiments, the polypeptides are at least about 12 amino acids in length.

As used herein, a "derivative" of a polypeptide or polynucleotide refers to a molecule having one, some or all amino acids or nucleic acids in the indicated sequence substituted with a non-natural derivative of the indicated amino acid or nucleic acid.

The term "nucleic acid" or "polynucleotide" refers to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides.

As used herein, a "heterologous molecule" is not identical to the reference molecule, nor is it, in the context of polypeptides and polynucleotides, an adjacent native sequence with respect to the reference molecule. Heterologous molecules are not limited to polypeptides and polynucleotides. Representative examples of heterologous molecules that can serve as cargo to be transported in accordance with the invention include, but are not limited to, small molecules, antibodies, drugs, contrast agents, vectors, and "attachment domains", such as biotin, or another peptide sequence, that attaches to a drug.

As used herein, "small molecule" refers to a low molecular weight organic compound having a molecular weight of less than 2000 Daltons, in some embodiments less than 1000 Daltons, and in still other embodiments less than 500 Daltons or less. A small molecule is typically between about 300 and about 700 Daltons. In a typical embodiment, a small molecule for use with the invention binds with high affinity to a protein, nucleic acid molecule, or a polysaccharide and alters the activity or function of the biopolymer to which it binds. Such molecules include, for example, heterocyclic compounds, carboxylic compounds, sterols, amino acids, lipids, and nucleic acids.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, a "delivery vehicle" or "carrier" means an element capable of carrying any type of cargo, such as small molecules, imaging agents, proteins, peptides, etc. For example, a delivery vehicle can be a polymer, nanoparticle or peptide carrier, and used for drugs or other cargo, and that can be attached to the peptide sequence for delivery.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

The term "antibody" is used in the broadest sense and specifically covers single monoclonal antibodies and antibody compositions with polyepitopic specificity. The term "monoclonal antibody" (mAb) as used herein refers to an antibody obtained from a population of substantially homogeneous antibodies, i.e. the antibodies comprising the individual population are identical except for possible naturally-occurring mutations that may be present in minor amounts.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline.

Compositions comprising such carriers are formulated by well known conventional methods (see, for example, *Remington's Pharmaceutical Sciences,* 18th edition, A. Gennaro, ed., Mack Publishing Co., Easton, Pa., 1990).

As used herein, "a" or "an" means at least one, unless clearly indicated otherwise.

Transport Peptides

Transport peptides as described herein may be of any length. Typically, the transport peptide will be between 6 and 50 amino acids in length, more typically between 10 and 20 amino acids in length. Transport peptides include the following. Optionally, the transport peptide further includes flanking sequence to facilitate incorporation into a delivery construct or carrier. In one embodiment, the peptide is flanked with cysteines. The transport peptides listed in the table below are shown with and without a flanking sequence for cyclization for use with phage. The transport peptide without flanking sequence is sometimes referred to as the "core" peptide. The core peptide can comprise as few as two amino acids.

| Clone/Name | Amino Acid Sequence* | With Flanking Sequence | SEQ ID NO: |
|---|---|---|---|
| 2404/TAxI | QSQSQMR | **SAC**QSQSQMR**CGGG** | 1; 8 |
| TAxI-Q | ASGAQAR | **GGC**ASGAQAR**CGG** | 2; 9 |
| 8a | PF | **SAC**PF**CGGG** | 3; 10 |
| 0808 | LQATPSA | **SAC**LQATPSA**CGGG** | 4; 11 |
| 2407 | ISPSLSS | **SAC**ISPSLSS**CGGG** | 5: 12 |
| 4802 | TSTGFRG | **SAC**TSTGFRG**CGGG** | 6; 13 |
| 4042 | TSTAPHLRLRLTSR | Not applicable | 7 |

*Each amino acid recited in these sequences may optionally be substituted with a non-natural derivative of the indicated amino acid.

In some embodiments, the peptide further comprises additional sequence selected to facilitate delivery into nuclei. For example, a peptide that facilitates nuclear delivery is a nuclear localizing signal (NLS). Typically, this signal consists of a few short sequences of positively charged lysines or arginines, such as PPKKRKV (SEQ ID NO: 14). In one embodiment, the NLS has the amino acid sequence PKKRKV (SEQ ID NO:15).

Peptides for use as transport peptides can be linear or cyclic. Cyclic peptide structures can be constructed for use in the invention. Representative approaches for cyclizing transport peptides include: use of flanking cysteines that form disulfide bonds, terminus cyclization or lactam bridges. Peptides may be N- or C-terminus modified to enhance peptide stability. Peptides are typically synthesized using solid phase or solution phase synthesis.

In some embodiments, the peptide comprises D-amino acids, β-amino acids, other non-natural amino acids, and/or has been structurally modified to enhance its utility for a given purpose. In some embodiments, the peptide comprises chemically modified amino acids.

Those skilled in the art will appreciate that certain variants thereof will be useful in the methods of the invention. A peptide "variant," as used herein, is a peptide that differs from a native transport peptide in one or more substitutions, deletions, additions and/or insertions, such that the transport activity of the peptide is not substantially diminished. In other words, the ability of a variant to undergo retrograde axonal transport may be enhanced or unchanged, relative to the native peptide, or may be diminished by less than 50%, and preferably less than 20%, relative to the native peptide. Such variants may generally be identified by modifying one of the above peptide sequences and evaluating the activity of the modified peptide using assays as described herein. Peptide variants preferably exhibit at least about 85%, more preferably at least about 90% and most preferably at least about 95% identity (determined as described above) to the identified peptides.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the peptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant peptides differ from a native sequence by substitution, deletion or addition of five amino acids or fewer.

Recombinant peptides encoded by DNA sequences as described herein may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant peptide. Suitable host cells include prokaryotes, yeast and higher eukaryotic cells. Preferably, the host cells employed are *E. coli*, yeast, insect cells or a mammalian cell line such as COS or CHO. Supernatants from suitable host/vector systems that secrete recombinant protein or peptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant peptide.

Portions and other variants having fewer than about 50 amino acids may also be generated by synthetic means, using techniques well known to those of ordinary skill in the art. In some embodiments, polypeptides of 6-50 amino acids in length are preferred, with lengths of 10-20 amino acids particularly suited to some uses. Such peptides may be synthesized using any of the commercially available solid-phase techniques, such as the Merrifield solid-phase synthesis method, where amino acids are sequentially added to a growing amino acid chain. See Merrifield, J. Am. Chem. Soc. 85:2149-2146, 1963. Equipment for automated synthesis of peptides is commercially available from suppliers such as Perkin Elmer/Applied BioSystems Division (Foster City, Calif.), and may be operated according to the manufacturer's instructions.

Peptides can be synthesized on a Perkin Elmer/Applied Biosystems Division 430A peptide synthesizer using FMOC chemistry with HPTU (O-BenzotriazoleN,N,N',N'-tetramethyluroniumhexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid: ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%-60% acetonitrile (containing 0.1%

TFA) in water may be used to elute the peptides. Following lyophilization of the pure fractions, the peptides may be characterized using electrospray or other types of mass spectrometry and by amino acid analysis.

In general, peptides (including fusion proteins) and polynucleotides as described herein are isolated. An "isolated" peptide or polynucleotide is one that is removed from its original environment. For example, a naturally occurring protein is isolated if it is separated from some or all of the coexisting materials in the natural system. Preferably, such peptides are at least about 90% pure, more preferably at least about 95% pure and most preferably at least about 99% pure. A polynucleotide is considered to be isolated if, for example, it is cloned into a vector that is not a part of the natural environment.

Antibodies

The term "antibody" is used in the broadest sense and specifically covers single monoclonal antibodies and antibody compositions with polyepitopic specificity. The term "monoclonal antibody" (mAb) as used herein refers to an antibody obtained from a population of substantially homogeneous antibodies, i.e. the antibodies comprising the individual population are identical except for possible naturally-occurring mutations that may be present in minor amounts.

The invention provides antibodies that bind to target proteins. The most preferred antibodies will specifically bind to a target and will not bind (or will bind weakly) to non-target counterparts. Antibodies that are particularly contemplated include monoclonal and polyclonal antibodies as well as fragments containing the antigen binding domain and/or one or more complementarity determining regions of these antibodies. As used herein, an antibody fragment is defined as at least a portion of the variable region of the immunoglobulin molecule that binds to its target, i.e., the antigen binding region.

Antibodies of the invention may be particularly useful in therapeutic strategies. Intracellularly expressed antibodies (e.g., single chain antibodies) may be therapeutically useful in treating conditions in which the expression of a target protein is involved.

An antibody or fragment thereof of the invention may be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. A second molecule for conjugation to the antibody can be selected in accordance with the intended use. Further, bi-specific antibodies specific for two or more epitopes may be generated using methods generally known in the art. Homodimeric antibodies may also be generated by cross-linking techniques known in the art (e.g., Wolff et al., Cancer Res. 53: 2560 2565).

Polynucleotides of the Invention

The invention provides polynucleotides that encode one or more transport peptides. Preferred polynucleotides comprise at least 15 consecutive nucleotides, preferably at least 30 consecutive nucleotides and more preferably 35 consecutive nucleotides, that encode a transport peptide. Polynucleotides that are fully complementary to any such sequences are also encompassed by the present invention. Polynucleotides may be single-stranded (coding or antisense) or double-stranded, and may be DNA or RNA molecules. Additional coding or non-coding sequences may, but need not, be present within a polynucleotide of the present invention, and a polynucleotide may, but need not, be linked to other molecules and/or support materials.

Representative Nucleic Acid Sequences:

| Name | DNA Sequence | SEQ ID NO: |
|---|---|---|
| 2404/TAxI | TCTGCTTGTCAGTCTCAGTCTCAGATG CGGTGCGGTGGAGGT | 16 |
| TAxI-Q | GGTGGTTGTGCTTCTGGTGCTCAAGCT CGTTGTGGTGGT | 17 |
| 8a | TCTGCTTGTCCTTTTTGTGGTGGTGGT | 18 |
| 4042 | ACCTCCACCGCACCGCATCTGAGACTG AGACTGACAAGCAGA | 19 |

Polynucleotides may comprise a native sequence (i.e., a sequence that encodes a transport peptide as described above or a portion thereof) or may comprise a variant of such a sequence, or an aptamer. Polynucleotide variants contain one or more substitutions, additions, deletions and/or insertions such that activity (including transport or specific binding, as appropriate) of the encoded peptide is not diminished, relative to a native peptide. Variants preferably exhibit at least about 60% identity, more preferably at least about 80% identity and most preferably at least about 90% identity to a polynucleotide sequence that encodes a native peptide or a portion thereof.

Two polynucleotide or peptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor. 11:105; Santou, N., Nes, M. (1987) Mol. Biol. Evol. 4:406-425; Sneath, P. H. A. and Sokal, R. R. (1973) Numerical Taxonomy the Principles and Practice of Numerical Taxonomy, Freeman Press, San Francisco, Calif.; Wilbur, W. J. and Lipman, D. J. (1983) Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or peptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native protein (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a peptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides may be prepared using any of a variety of techniques known in the art, including, for example, oligonucleotide synthesis. Libraries can be screened with probes designed to identify the gene of interest or the peptide encoded by it. Screening the cDNA or other library with the selected probe may be conducted using standard procedures, such as those described in Sambrook et al., *Molecular Cloning: A Laboratory Manual* (New York: Cold Spring Harbor Laboratory Press, 1989).

The oligonucleotide sequences selected as probes should be sufficiently long and sufficiently unambiguous that false positives are minimized. The oligonucleotide is preferably labeled such that it can be detected upon hybridization to DNA in the library being screened. Methods of labeling are well known in the art, and include the use of radiolabels, such as $^{32}$P-labeled ATP, biotinylation or enzyme labeling. Hybridization conditions, including moderate stringency and high stringency, are provided in Sambrook et al., supra.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., DNA 2:183, 1983). Alternatively, RNA molecules may be generated by in vitro or in vivo transcription of DNA sequences encoding a transport peptide, or portion thereof, provided that the DNA is incorporated into a vector with a suitable RNA polymerase promoter (such as T7 or SP6). Certain portions may be used to prepare an encoded peptide, as described herein. In addition, or alternatively, a portion may be administered to a patient such that the encoded peptide is generated in vivo (e.g., by transfecting antigen-presenting cells, such as dendritic cells, with a cDNA construct encoding a transport peptide, and administering the transfected cells to the patient).

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine. Aptamers, oligonucleotides that recognize and bind to specific protein surfaces and therefore can interfere with the protein activity of a target, are typically modified for therapeutic use. Where rapid clearance is desired, however, non-modified aptamers can be used in methods of the invention.

Nucleotide sequences can be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and to permit expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art. Some embodiments of the peptides of the invention have been described herein with a cell penetrating peptide (CPP) incorporated into the peptide for facilitation of entry into a cell.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Antisense and Inhibitory Nucleic Acid Molecules

The antisense molecules of the present invention comprise a sequence substantially complementary, or preferably fully complementary, to all or a fragment of a nucleic acid molecule that encodes a protein to be targeted, e.g., for reduced expression. Included are fragments of oligonucleotides within a coding sequence, and inhibitory nucleotides that inhibit the expression of targeted proteins. Antisense oligonucleotides of DNA or RNA complementary to sequences at the boundary between introns and exons can be employed to prevent the maturation of newly-generated nuclear RNA transcripts of specific genes into mRNA for transcription. Antisense RNA, including siRNA, complementary to specific genes can hybridize with the mRNA for that gene and prevent its translation. Other antisense nucleic acid molecules can be used to disrupt expression, such as ribozymes. The antisense molecule can be DNA, RNA, or a derivative or hybrid thereof, such as a chimeric gapmer. Examples of such derivative molecules include, but are not limited to, peptide nucleic acid (PNA) and phosphorothioate-based molecules such as deoxyribonucleic guanidine (DNG) or ribonucleic guanidine (RNG).

The antisense molecules of the invention are complementary to nucleic acid sequences that encode a target protein. The degree of homology necessary will depend on the particular polynucleotide of the invention. A homology of at least about 60% is sufficient for siRNAs, while larger antisense molecules and PCR primers require a homology of about 70% or greater.

Antisense RNA can be provided to the cell as "ready-to-use" RNA synthesized in vitro or as an antisense gene stably transfected into cells that will yield antisense RNA upon transcription. Hybridization with mRNA results in degradation of the hybridized molecule by RNAse H and/or inhibition of the formation of translation complexes. Both result in a failure to produce the product of the original gene.

Both antisense RNA and DNA molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro or in vivo transcription of DNA sequences encoding the antisense RNA molecule. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

The design of siRNA molecules is known in the art and can be provided by vendors (e.g., Applied Biosystems/Ambion, Austin, Tex.). Beginning with the AUG start codon of the transcript, one can begin by scanning for AA dinucleotide sequences. Each AA and the 3' adjacent 19 nucleotides can be identified as potential siRNA target sites. This strategy for choosing siRNA target sites is based on the observation by Elbashir et al. (2001, EMBO J 20: 6877-6888) that siRNAs with 3' overhanging UU dinucleotides are the most effective. This is also compatible with using RNA pol III to transcribe hairpin siRNAs because RNA pol III terminates transcription at 4-6 nucleotide poly(T) tracts creating RNA molecules with a short poly(U) tail. In some embodiments, the selection of the siRNA target sequence is purely empirically determined, as long as the target sequence starts with GG and does not share significant sequence homology with other genes as analyzed by BLAST search. Alternatively, any accessible site in endogenous mRNA can be targeted for degradation by the synthetic oligodeoxyribonucleotide/RNase H method (Lee, K. S., et al. (2002) Nature Biotechnology 20: 500-505). Any accessible site identified in this fashion is then used as insert sequence in the U6 promoter-driven siRNA constructs. Typically, the siRNA expression cassette has a stem length of 19 nucleotides. siRNA stems ranging from 21 nucleotides-long to 25-29 nucleotides-long can also be useful in gene silencing.

DNA molecules may be modified to increase intracellular stability and half-life. Possible modifications include, but are not limited to, the addition of flanking sequences of the 5' and/or 3' ends of the molecule or the use of phosphorothioate or 2' O-methyl rather than phosphodiesterase linkages within the backbone of the molecule. Other modifications include the use of chimeric antisense compounds. Chimeric antisense compounds of the invention may be formed as composite structures of two or more oligonucleotides, modified oligonucleotides, oligonucleosides and/or oligonucleotide mimetics. Such compounds have also been referred to in the art as hybrids or gapmers. Representative United States patents that teach the preparation of such hybrid structures include, but are not limited to, U.S. Pat. Nos. 5,700,922 and 6,277,603.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Antisense compositions of the invention include oligonucleotides formed of homopyrimidines that can recognize local stretches of homopurines in the DNA double helix and bind to them in the major groove to form a triple helix. See: Helen, C and Toulme, J J. Specific regulation of gene expression by antisense, sense, and antigene nucleic acids. Biochem. Biophys Acta, 1049:99-125, 1990. Formation of the triple helix would interrupt the ability of the specific gene to undergo transcription by RNA polymerase. Triple helix formation using myc-specific oligonucleotides has been observed. See: Cooney, M, et al. Science 241:456-459.

Antisense sequences of DNA or RNA can be delivered to cells. Several chemical modifications have been developed to prolong the stability and improve the function of these molecules without interfering with their ability to recognize specific sequences. These include increasing their resistance to degradation by DNases, including phosphotriesters, methylphosphonates, phosphorothioates, alpha-anomers, increasing their affinity for binding partners by covalent linkage to various intercalating agents such as psoralens, and increasing uptake by cells by conjugation to various groups including polylysine. These molecules recognize specific sequences encoded in mRNA and their hybridization prevents translation of and increases the degradation of these messages.

Antisense compositions including oligonucleotides, derivatives and analogs thereof, conjugation protocols, and antisense strategies for inhibition of transcription and translation are generally described in: Antisense Research and Applications, Crooke, S, and B. Lebleu, eds. CRC Press, Inc. Boca Raton Fla. 1993; Nucleic Acids in Chemistry and Biology Blackburn, G. and M. J. Gait, eds. IRL Press at Oxford University Press, Inc. New York 1990; and Oligonucleotides and Analogues: A Practical Approach Eckstein, F. ed., IRL Press at Oxford University Press, Inc. New York 1991; which are each hereby incorporated herein by reference including all references cited therein which are hereby incorporated herein by reference.

Pharmaceutical Compositions

The invention provides transport peptides, peptidomimetics, and/or polynucleotides that are incorporated into pharmaceutical compositions. Pharmaceutical compositions comprise one or more such compounds and, optionally, a physiologically acceptable carrier. Pharmaceutical compositions within the scope of the present invention may contain other compounds that may be biologically active or inactive. For example, one or more portions of other biologically active molecules may be present, either incorporated into a fusion polypeptide or as a separate compound, within the composition.

A pharmaceutical composition can contain DNA encoding one or more of the peptides as described above, such that the peptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, Crit. Rev. Therap. Drug Carrier Systems 15:143-198, 1998, and references cited therein. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface or secretes such an epitope.

In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., Proc. Natl. Acad. Sci. USA 86:317-321, 1989; Flexner et al., Ann. N.Y. Acad. Sci. 569:86-103, 1989; Flexner et al., Vaccine 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner-Biotechniques 6:616-627, 1988; Rosenfeld et al., Science 252:431-434, 1991; Kolls et al., Proc. Natl. Acad. Sci. USA 91:215-219, 1994; Kass-Eisler et al., Proc. Natl. Acad. Sci. USA 90:11498-11502, 1993; Guzman et al., Circulation 88:2838-2848, 1993; and Guzman et al., Cir. Res. 73:1202-1207, 1993. Techniques for incorporating DNA into such expression systems are well known to those of ordinary skill in the art. The DNA may also be "naked," as described, for example, in Ulmer et al., Science 259:1745-1749, 1993 and reviewed by Cohen, Science 259:1691-1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption of the delivered molecule. Such excipients are those substances usually and customarily employed to formulate dosages for parenteral administration in either unit dose or multi-dose form or for direct infusion into the CSF by continuous or periodic infusion from an implanted pump.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

The compositions described herein may be administered as part of a sustained release formulation (i.e., a formulation such as a capsule or sponge that effects a slow release of compound following administration, or other implantable device). Such formulations may generally be prepared using well known technology and administered by, for example, oral, rectal or subcutaneous implantation, or by implantation at the desired target site, such as within a muscle. Sustained-release formulations may contain a peptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Methods of Cargo Delivery to CNS

The invention provides methods of using the transport peptide for retrograde transport of cargo to the central nervous system (CNS). In some embodiments, the peptide transports cargo from a peripheral site to the CNS. Alternatively, the transport peptide can be delivered directly to the CNS and efficiently taken up by neurons or other target cells in the CNS. The method can be used to deliver cargo, or heterologous molecules, ranging in size from small molecules to peptides to substantial moieties, such as macromolecules and liposomes. In addition to small molecules or radioisotopes, cargo can be accommodated that is in the nanoparticle range, e.g. up to 5-10 nm, or, in some embodiments, up to 100-200 nm in size, or up to 500 nm in size, or larger.

In one embodiment, the invention provides a method of delivering a molecule to a CNS site of a subject. In another embodiment, the invention provides a method of treating a CNS condition in a subject. The method comprises administering the transport peptide, to which a heterologous molecule is attached, to the CNS or to a peripheral site of the subject. In one example, the transport peptide and the heterologous molecule are then transported from the peripheral site to the spinal cord and/or other CNS location. In other example, the transport peptide and its cargo are delivered directly to the CNS, e.g., via intrathecal or epidural administration. In some embodiments, the transport peptide and its cargo are delivered trans-synaptically to interneurons, sensory neurons, and to higher CNS structures. The CNS site for delivery by the method is thus the spinal cord, ventral horn motor neurons, DRG, brain, motor cortex, sensory cortex, basal ganglia, and other structures of the forebrain (including the cerebrum, thalamus and hypothalamus) and basal forebrain, midbrain (including the tectum and tegmentum), or hindbrain (including the pons, cerebellum, and medulla oblongata).

The cargo for delivery, the heterologous molecule, which can optionally be a delivery vehicle containing the heterologous molecule, can be attached to the transport peptide using any of a variety of conventional techniques known to those skilled in the art, such as by chemical conjugation (see Hermanson, *Bioconjugate Techniques*, Elsevier 1996), electrostatic interaction, non-covalent affinity interactions, or expression as a fusion partner. In one embodiment, the transport peptide is a fusion protein comprising the transport peptide fused with a heterologous peptide. Examples of heterologous peptides include, but are not limited to, enzymes, growth factors, antibodies, and therapeutic peptides.

Representative examples of the heterologous molecule include, but are not limited to, a polypeptide, antibody, polynucleotide, vector, small molecule, drug, contrast agent, delivery vehicle, and or an attachment domain. Delivery vehicles include, for example, viruses, polymer carriers, and peptide carriers. Contrast agents include, for example, an optical contrast agent or other agent useful for magnetic resonance imaging (MRI) or positron emission tomography (PET). Representative examples of polypeptides for use with the invention include, but are not limited to, survival motor neuron (SMN) protein, glial-derived neurotrophic factor (GDNF), brain-derived neurotrophic factor (BDNF), fibroblast growth factor (FGF), vascular endothelial growth factor (VEGF), nerve growth factor (NGF), neurotrophin (NT), transforming growth factor (TGF), ciliary neurotrophic factor (CNTF), epidermal growth factor (EGF), insulin-like growth factor (IGF), stromal cell factor (SCF), notch, heparan sulfate proteoglycans (HSPGs) and growth factors within these classes such as, for example, NT-3, NT-4/5, NT-6, IGF-1, IGF-2, bFGF, neurturin, persephin, artemin, TGFα, TGFβ, PDGF, FGF-2, SCF-1 and BMP, FGF20, VIP, and pleiotrophin (PTN).

In addition to the above examples of polypeptides as heterologous molecules for delivery via a transport peptide of the invention, antibodies and functional fragments thereof are contemplated. Conventional antibodies and fragments thereof, as well as intrabodies (IAbs), can be used in a therapeutic context. For example, a transport peptide of the invention can be used to deliver one or more antibodies to slow or halt disease progression. Antibodies targeting tau and/or beta-amyloid protein (bap), for example, can be used to slow progression of Alzheimer's disease. Antibodies targeting α-synuclein, as another example, can be used to treat Parkinson's disease. The onset or progression of Huntington's disease may be delayed by treatment with antibodies targeting mutant Huntingtin protein. labs, intracellularly expressed antibody fragments consisting only of antigen recognition domain(s), can be designed to recognize either distinct conformations or distinct epitopes in proteins that cause neurodegenerative diseases. Examples of epitope-specific intrabody therapies being developed for treatment of Alzheimer's disease, Huntington's disease and Parkinson's disease are described in Southwell and Patterson, 2010, *Reviews in the Neurosciences* 21, 273-287.

Representative polynucleotides suitable for use with the invention include, but are not limited to, antisense polynucleotides, such as ribozymes and small interfering RNA (siRNA) molecules as well as other RNA-based therapeutics (see, e.g., Kole et al., 2012, *Nat Rev Drug Discov.*, 11(2):125-40). Some examples of siRNAs that can be used to treat neurodegenerative diseases are described in U.S. Pat. No. 7,829,694, and include those which: target the mRNA for the α-synuclein protein in order to reduce the amount of α-synuclein protein produced in neurological cells to treat Parkinson's disease; target the mRNA for BACE1 (including variants thereof, e.g. variants A, B, C, and D) in order to reduce the amount of BACE1 (including variants thereof, e.g. variants A, B, C, and D) protein produced in neurological cells and thereby interfere with the production of beta-amyloid to treat Alzheimer's disease; target the mRNA for huntingtin protein to reduce the amount of mutant huntingtin protein produced in neurological cells to treat Hungtington's disease; target the mRNA for ataxin1 protein to reduce the amount of ataxin1 protein produced in neurological cells to treat Spinocerebellar Ataxia Type 1; target the mRNA for ataxin3 protein to reduce the amount of ataxin3 protein produced in neurological cells to treat Spinocerebellar Ataxia Type 3; target the mRNA for atrophin-1 protein to reduce the amount of atrophin-1 protein produced in neurological cells to treat dentatorubral-pallidoluysian atrophy (DRPLA).

Therapeutic and Prophylactic Methods

Treatment includes prophylaxis and therapy. Prophylaxis or therapy can be accomplished by a single direct injection at a single time point or multiple time points to a single or multiple sites. Administration can also be nearly simultaneous to multiple sites. Patients or subjects include mammals, such as human, bovine, equine, canine, feline, porcine, and ovine animals. The subject is preferably a human.

Peptides or nucleic acid based drugs (e.g., antisense RNAs, siRNAs, mRNAs) can be delivered to cells via chemical means, biological means, carrier peptides, vectors, or physical delivery systems. Representative chemical means include, but are not limited to, specific chemical substances, including cationic polymers such as polyethylenimine (PEI) and cationic lipids. An example of a biological means of delivery is cell-penetrating peptides (CPPs). An exemplary carrier peptide is transportan. Vectors include plasmids and viruses, or cells. Representative physical delivery systems include, but are not limited to electrically-based systems and those using mechanical force, such as gene guns.

Conditions to be treated include, but are not limited to, a neurodegenerative disease, stroke, injury or chronic pain. Neurodegenerative diseases are characterized by a progressive loss of structure and/or function of neurons, glial cells, and/or neural structures. Examples of diseases or conditions to be treated include spinal muscular atrophy (SMA), Parkinson's disease, Alzheimer's disease, Huntington's disease, spinocerebellar ataxia, Friedreich's ataxia, amyotrophic lateral sclerosis (ALS), progressive muscular atrophy (PMA), progressive bulbar palsy (PBP), primary lateral sclerosis (PLS), Creutzfeldt-Jakob disease, primary progressive aphasia, Lewy body disease, and progressive supranuclear palsy.

Administration and Dosage

The compositions are administered in any suitable manner, optionally as pharmaceutically acceptable salts or with pharmaceutically acceptable carriers. Suitable methods of administering compositions, moieties, and molecules in the context of the present invention to a subject are available, and, although more than one route can be used to administer a composition, a particular route can often provide a more immediate and more effective reaction than another route.

The dose administered to a patient, in the context of the present invention, should be sufficient to effect a beneficial therapeutic response in the patient over time, to delay onset of disease, or to inhibit disease progression. Thus, the composition is administered to a subject in an amount sufficient to alleviate, reduce, and cure or at least partially delay or arrest symptoms and/or complications from the disease. An amount adequate to accomplish this is defined as a "therapeutically effective dose."

A suitable dose is an amount that, when administered as described herein, is capable of promoting a reduction in symptoms, and preferably at least 10-50% improvement over the basal (i.e., untreated) level. Such therapies should lead to an improved clinical outcome (e.g., more frequent remissions, complete or partial or longer disease-free survival) in patients as compared to untreated patients. In general, for pharmaceutical compositions comprising one or more peptides, the amount of each peptide present in a dose ranges from about 100 μg to 5 mg per kg of host. Suitable volumes will vary with the size of the patient, but will typically range from about 0.1 mL to about 5 mL.

Routes and frequency of administration of the therapeutic compositions disclosed herein, as well as dosage, will vary from individual to individual, and may be readily established using standard techniques. In general, the pharmaceutical compositions may be administered, by injection or implantation (e.g., intracutaneous, intratumoral, intramuscular, intraperitoneal, intravenous, intrathecal, epidural or subcutaneous), intranasally (e.g., by aspiration) or orally. Typically the administration is intramuscular, intraperitoneal, intrathecal or subcutaneous. In one example, between 1 and 10 doses may be administered over a 52 week period. Preferably, 6 doses are administered, at intervals of 1 month, and booster administrations may be given periodically thereafter, as indicated. Alternate protocols may be appropriate for individual patients. In one embodiment, 2 intradermal injections of the composition are administered 10 days apart. In another embodiment, a dose is administered daily or once every 2 or 3 days over an extended period, such as weeks or months.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients.

Kits

For use in the methods described herein, kits are also within the scope of the invention. Such kits can comprise a carrier, package or container that is compartmentalized to receive one or more containers such as vials, tubes, and the like, each of the container(s) comprising one of the separate elements to be used in the method. For example, the container(s) can comprise a transport moiety that is, optionally, detectably labeled. The transport moiety can be a transport peptide, or polynucleotide encoding a transport peptide, of the invention. Optionally, included in the same or a separate container, the kit comprises a cargo moiety attached or to be attached to the transport moiety. The kit can also include one or more containers for a reporter-means, such as a biotin-binding protein, e.g., avidin or streptavidin, bound to a detectable label, e.g., an enzymatic, florescent, or radioisotope label for use in monitoring transport of the peptide. The kit can include all or part of an amino acid sequence described herein, or a nucleic acid molecule that encodes such amino acid sequences.

The kit of the invention will typically comprise the container described above and one or more other containers comprising materials desirable from a commercial and user standpoint, including buffers, diluents, filters, needles, syringes, and package inserts with instructions for use. In addition, a label can be provided on the container to indicate that the composition is used for a specific therapeutic or non-therapeutic application, and can also indicate directions for either in vivo or in vitro use, such as those described above. Directions and or other information can also be included on an insert which is included with the kit.

EXAMPLES

The following examples are presented to illustrate the present invention and to assist one of ordinary skill in making and using the same. The examples are not intended in any way to otherwise limit the scope of the invention.

Example 1

Targeted Axonal Import (TAxI) Peptide Delivers Functional Proteins into the Spinal Cord after Peripheral Administration This example demonstrates a peptide capable of delivering protein complexes and proteins into the spinal cord motor neurons using targeted axonal import (TAxI). The TAxI peptide is shown to enhance bacteriophage accumulation in the soma of spinal cord motor neurons and enrich NeutrAvidin accumulation in the spinal cord and brain after intramuscular administration. Notably, TAxI-Cre recombinase fusion proteins induced selective recombination and tdTomato expression in motor neurons of reporter mice after intramuscular injections. This demonstration of motor neuron-targeted delivery of functional proteins to the CNS establishes the clinical potential of this technology for minimally invasive administration of CNS-targeted therapeutics.

Figure 1B:
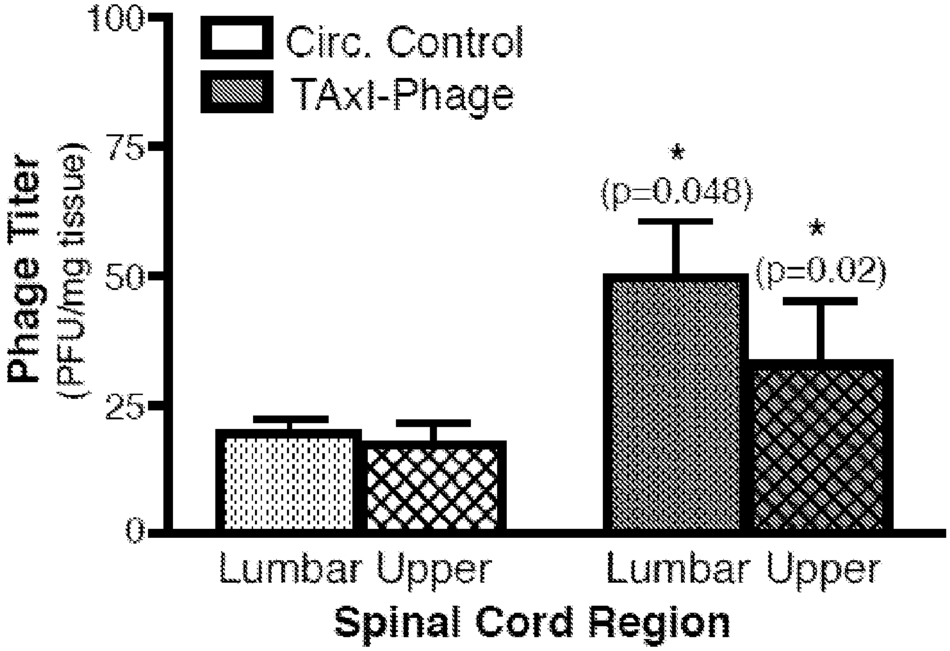

First, a strategy was developed to screen a recombinant phage display library in vivo to identify peptides that mediate delivery into the CNS via retrograde transport (FIG. 1*a*). Initially, a 50:50 mix of M13 bacteriophage libraries displaying linear and disulfide constrained peptide sequences were injected bilaterally into the gastrocnemius muscles of mice and phage were harvested from the spinal cord at three time points (8, 24, and 48 hours). This design allowed us to capture clones that would experience fast axonal transport as well as to avoid contamination from circulating phage, which takes 24 hours to clear from the blood supply.[23, 24] After three reiterative screens, DNA sequencing revealed five recurrent clones from tissue harvested 8-, 24-, and 48-hours post injection. Interestingly, only phage from the cyclic peptide library showed selection under this scheme. After amplification and purification, each recombinant clone was evaluated independently for delivery into the CNS after intramuscular (IM) injection. Clone 2404 produced the highest titer from lumbar spinal cord tissues. Increased spinal cord accumulation of clone 2404 compared to a control phage with a cyclized peptide insert was detected in both the lower (lumbar-sacral)

and upper (cervical-thoracic) spinal cord segments after a single IM injection (FIG. 1*b*), and as such was designated TAxI-phage.

Figure 2A:
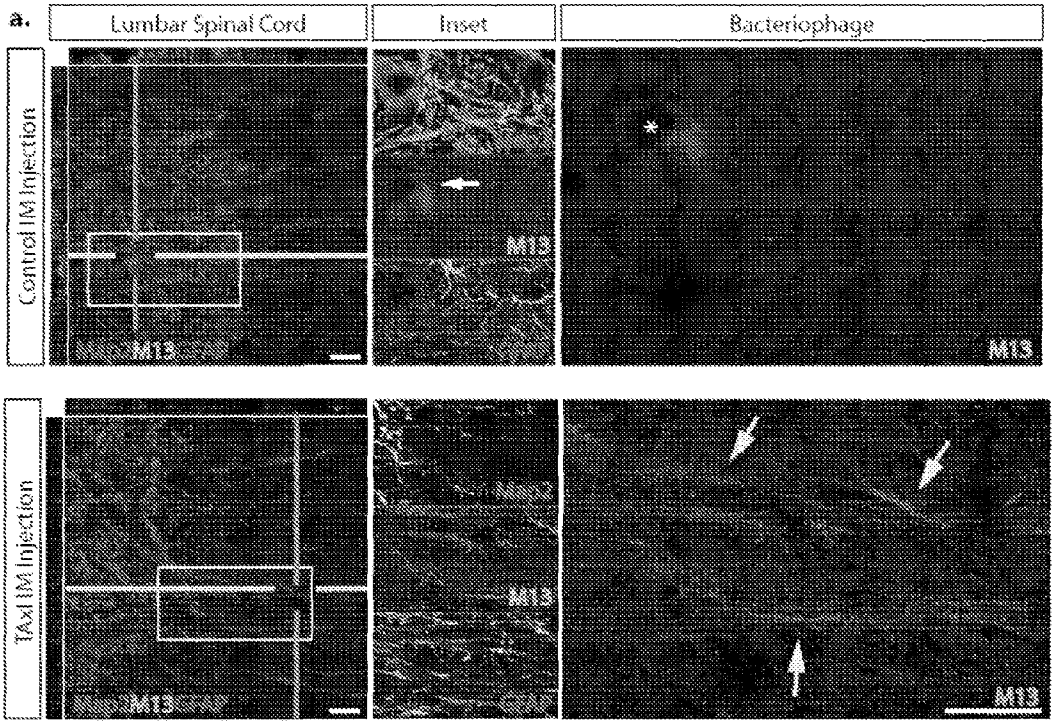
FIG. 2A-2B. Photomicrographs showing immunofluorescent localization of phage particles within the lumbar spinal cord.

To confirm phage targeting of spinal cord somatic motor neurons, spinal cord tissue isolated 24 hrs after an IM injection of recombinant phage was stained by immunofluorescence to examine the anatomical localization of control and TAxI-phage along cellular processes. Confocal microscopy revealed low levels of diffuse bacteriophage stain (M13 coat protein) around vascular lumen in the lumbar spinal cord of mice injected with control phage (FIG. 2*a*, top panels). Examination of individual phenotypic stains (inset) revealed that the control phage did not colocalize with astrocyte (GFAP) or neuronal markers (Map2) and only showed diffuse staining near the vasculature (expanded inset, *). In contrast, TAxI-phage showed filamentous $M13^+$-projections within the ventral aspects of the spinal cord in zones of ventral motor roots. M13 immunofluorescence colocalized along GFAP and Map2+ processes within TAxI-phage injected animals (inset), and higher magnifications showed it decorated long filamentous processes that projected from the ventral horn through the root entry zone (expanded inset; arrows), suggesting that TAxI-phage entered the spinal cord via somatic motor neurons possibly by transiting the axolemma.

Figure 2B:
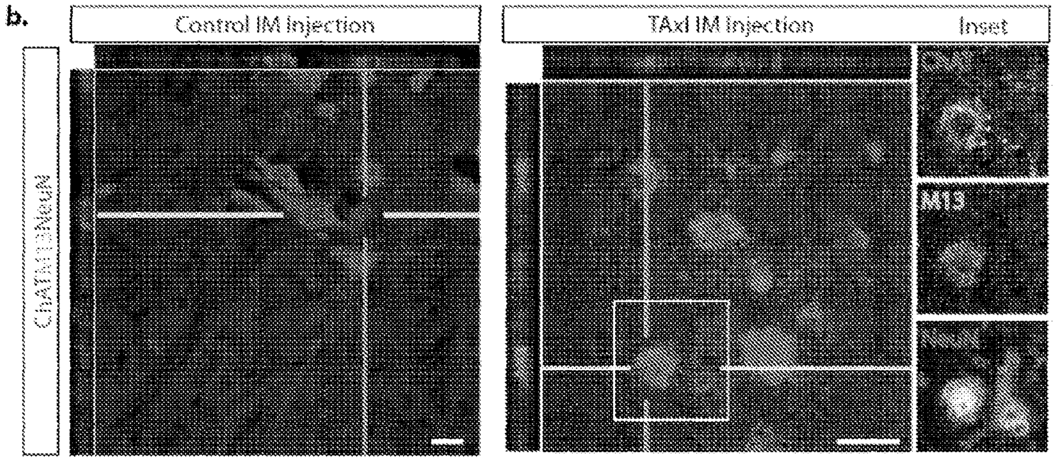

Somatic motor neurons are known to project axons from the spinal cord out to the neuromuscular junction. Therefore, to determine whether clone-2404 entered the spinal cord via motor neurons, lumbar spinal cord tissue was stained by immunofluorescence and analyzed for colocalization of phage with a motor neuron marker. Clone 2404 showed a distinct colocalization with cells within the ventral horn that stained positive for the motor neuron marker choline acetyltransferase (ChAT) and neuronal nuclear antigen (NeuN) (FIG. 2*b*). Control phage did not colocalize with either $NeuN^+$ or $ChAT^+$ cells. Together, these data reveal that TAxI-phage was able to target spinal cord motor neurons selectively after an injection into peripheral muscle and targeted axonal import (TAxI) to transit into the spinal cord.

Figure 3A:
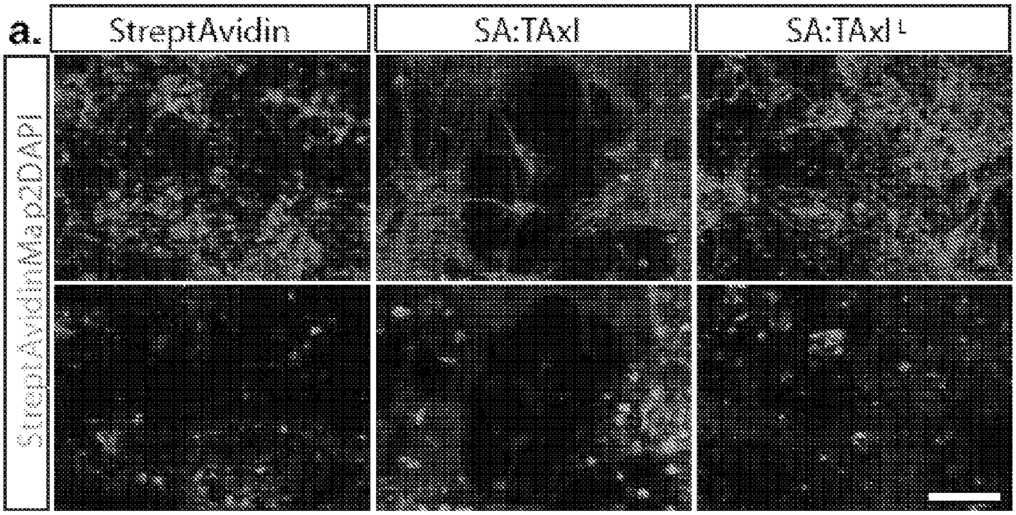
FIGS. 3A-3C. Illustrate distribution of peptide complexes after intramuscular injection in the gastrocnemius.
Figure 3B:
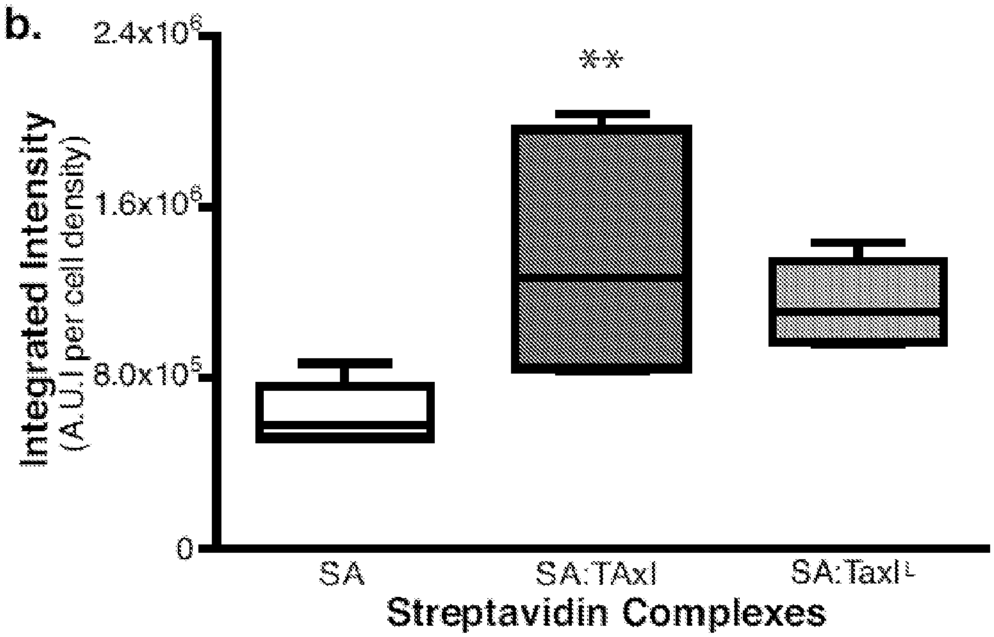

Next, we examined whether TaxI peptide could mediate neuronal uptake and delivery of macromolecular drugs. The TAxI sequence (SACQSQSQMRCGGG; SEQ ID NO: 8) was synthesized, biotinylated at the amino-terminus, and cyclized. In addition, a linearized control peptide, ($TAxI^L$, SAAQSQSQMRAGGG; SEQ ID NO: 20), with cysteines replaced by alanines) was synthesized and each peptide was complexed with the model protein streptavidin (SA). Fluorescently-labeled SA, SA:TAxI, and SA:$TAxI^L$ was incubated with primary neuron cultures isolated from cerebellum of neonatal mice (P6) for 30 minutes to determine neuron association and uptake. Both SA:TAxI and SA:$TAxI^L$ showed uptake into cell bodies (FIG. 3*a*), but only SA:TAxI showed a significant increase above baseline fluorescence compared to primary neurons (FIG. 3*b*). However, with a 60-minute incubation, SA:$TAxI^L$ also showed a significant increase above controls, indicating that linearized peptide is able to mediate neuronal uptake, but the secondary structure imparted by the cysteine residues is needed for efficient uptake of the SA-complexes.

Figure 3C:
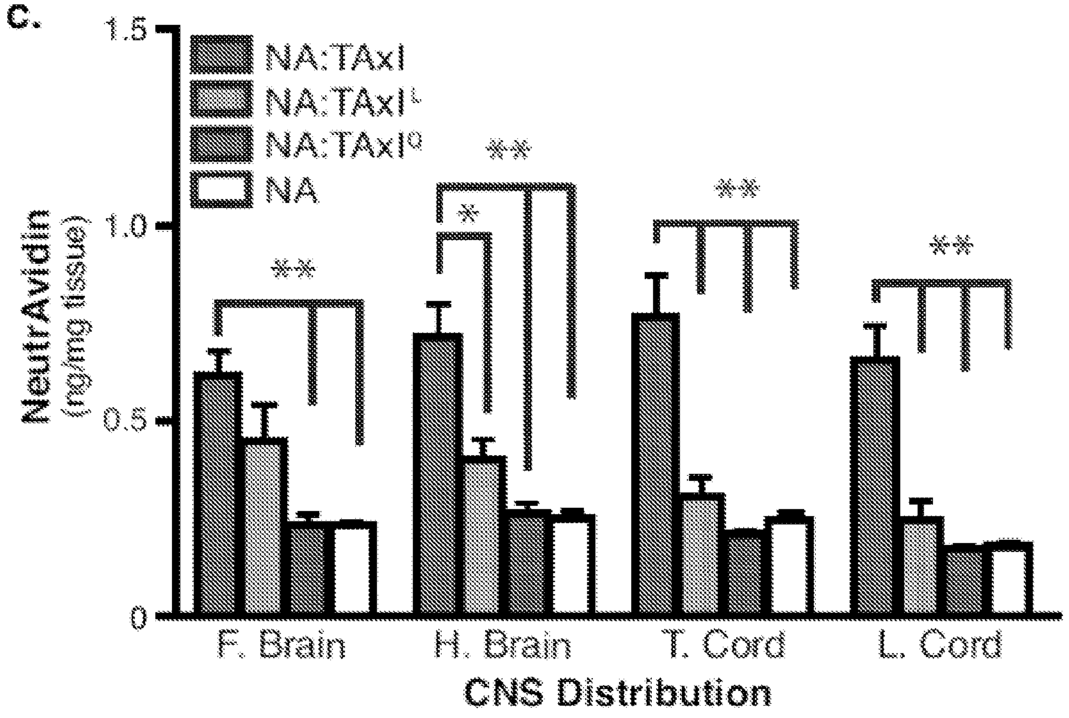

Following the demonstrated uptake of the SA:TAxI by primary neurons, we tested whether the TAxI peptide could mediate protein delivery into the CNS. For this, NeutrAvidin (NA), the biotin-binding protein with the least non-specific binding, was used as a model protein. Since $TAxI^L$ displayed less efficient but still observable binding and uptake in primary neurons, an additional control cyclic peptide ($TAxI^Q$, GGCASGAQARCGGG; SEQ ID NO: 9) was synthesized that scrambled the TAxI sequence and replaced two glutamine residues with alanines. NA:TAxI, NA:$TAxI^L$, NA:$TAxI^Q$ and NA were injected into the gastrocnemius of mice and major organs harvested 24 hours after injection. ELISA was used to determine the biodistribution of NeutrAvidin. Attachment of TAxI increased distribution of NA to the brain and spinal cord by 3- and 3.5-fold, respectively (FIG. 3*c*). NA-TAxI was enriched throughout the hindbrain, forebrain, thoracic-cervical and lumbar-sacral spinal cord. NA:$TAxI^L$ showed moderate accumulation in brain but to a lesser extent compared to NA:TAxI, and NA:$TAxI^Q$ showed a distribution similar to NA in vital organs. Thus, the TAxI peptide significantly increased NeutrAvidin distribution into the CNS greatly after bi-lateral injections into the gastrocnemius.

Figure 4A:
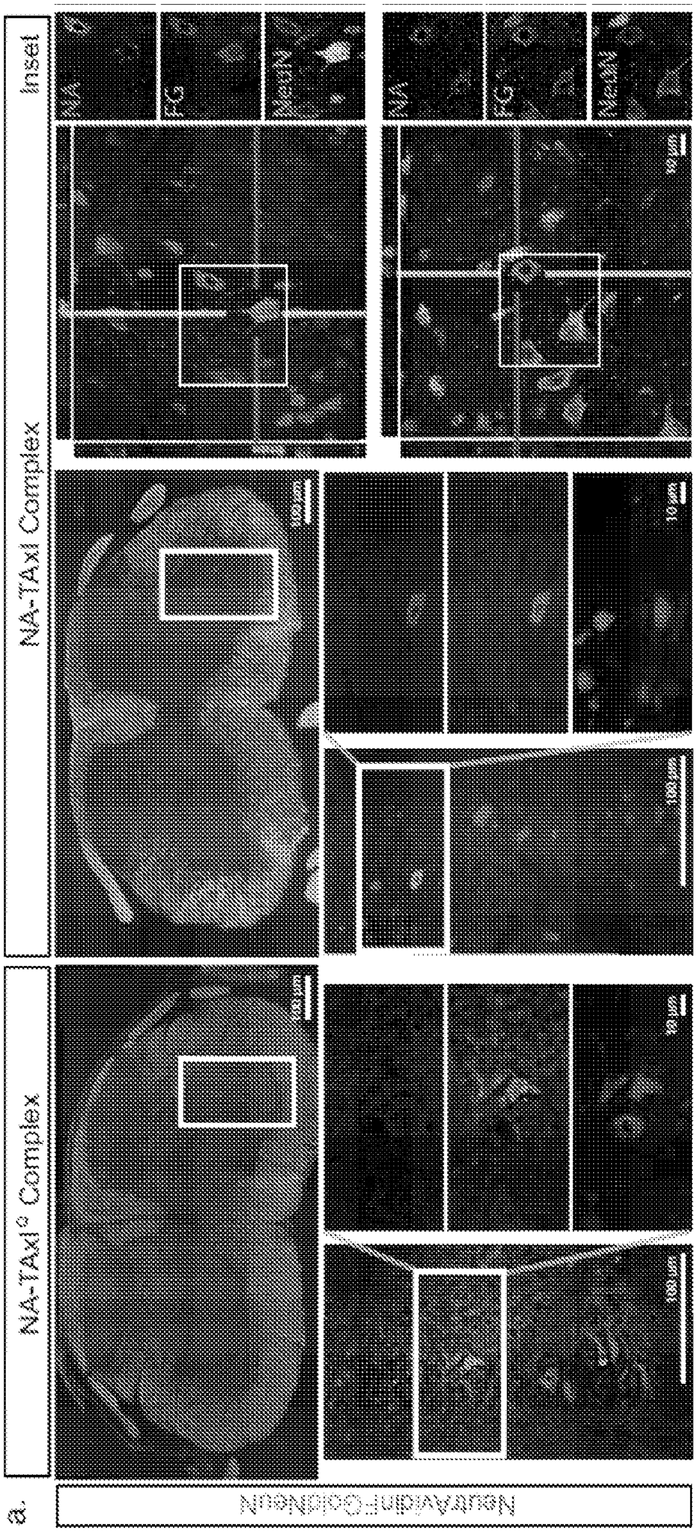
FIGS. 4A-4B. Illustrate neutrAvidin peptide complex delivery to the spinal cord along traced axons after IM injection in the gastrocnemius. Fluoro-Gold was injected into the gastrocnemius to trace motor neurons in the spinal cord that project to peripheral muscles.

We next tested our hypothesis that the TAxI peptide can be used to target somatic motor neurons selectively. Segment-specific lower motor neurons were therefore pre-labeled by unilateral IM injection of Fluorogold, which has been shown to trace peripheral axons back to the spinal cord.[25] Seven days after Fluorogold administration, NA, NA:$TAxI^Q$, and NA:TAxI complexes were administered intramuscularly by bilateral injection followed by saline perfusion and fixation after 24 hours. Spinal cord sections were stained by immunofluorescence to visualize NA within the ventral horns. As observed previously, NA:$TAxI^Q$ immunofluorescence was sparse and did not colocalize with Fluorogold within the ventral horns. In contrast, NA:TAxI complexes localized predominantly with the neuronal marker NeuN. In particular, NA:TAxI was found to colocalize with multiple Fluorogold-labeled $NeuN^+$-neurons in the ipsilateral horn (FIG. 4*a*) as well as a noticeable and pronounced distribution amongst NeuN motor neurons within the contralateral ventral horn.

Figure 4B:
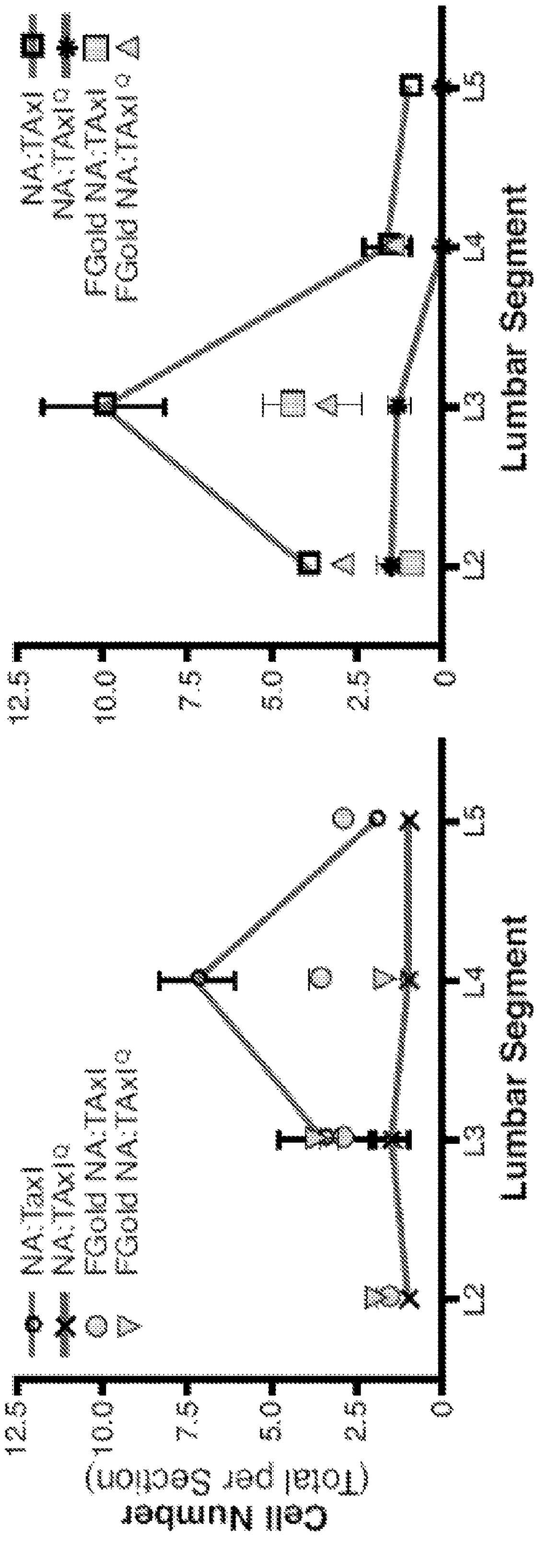

Due to the observed localization of NA:TAxI complexes in multiple neurons within the ventral grey matter (FIG. 4*a*, insets), we quantified the longitudinal distribution of NA to profile the frequency-distribution of NA-complexes within the lumbar spinal cord. We counted NA- and Fluorogold-labeled neurons within in serial sections (120 μm separation, N=3) of lumbar segments (1 mm interval) from mice injected with NA:TAxI and NA:$TAxI^Q$ protein complexes. As with previous experiments, the number of NA-labeled cells was low in NA:$TAxI^Q$ injected animals (FIG. 4*b*). In stark contrast, animal injected with NA-TAxI complexes had numerous neurons labeled with NA and Fluorogold throughout the lumbar spinal cord with a distinct spike at ~L3/L4, which correlates anatomically with the segments innervated by the sciatic nerve.[26] In addition, the trend of NA distribution correlated with Fluorogold (~2:1; bilateral injection of NA versus unilateral injection of Fluorogold, respectively) (FIG. 4*b*. replicates shown). Together, these data demonstrate that the TAxI peptide is able to mediate and target axonal import for protein delivery into the CNS via retrograde transport along efferent motor neurons at peripheral neuromuscular junctions.

Figure 5:
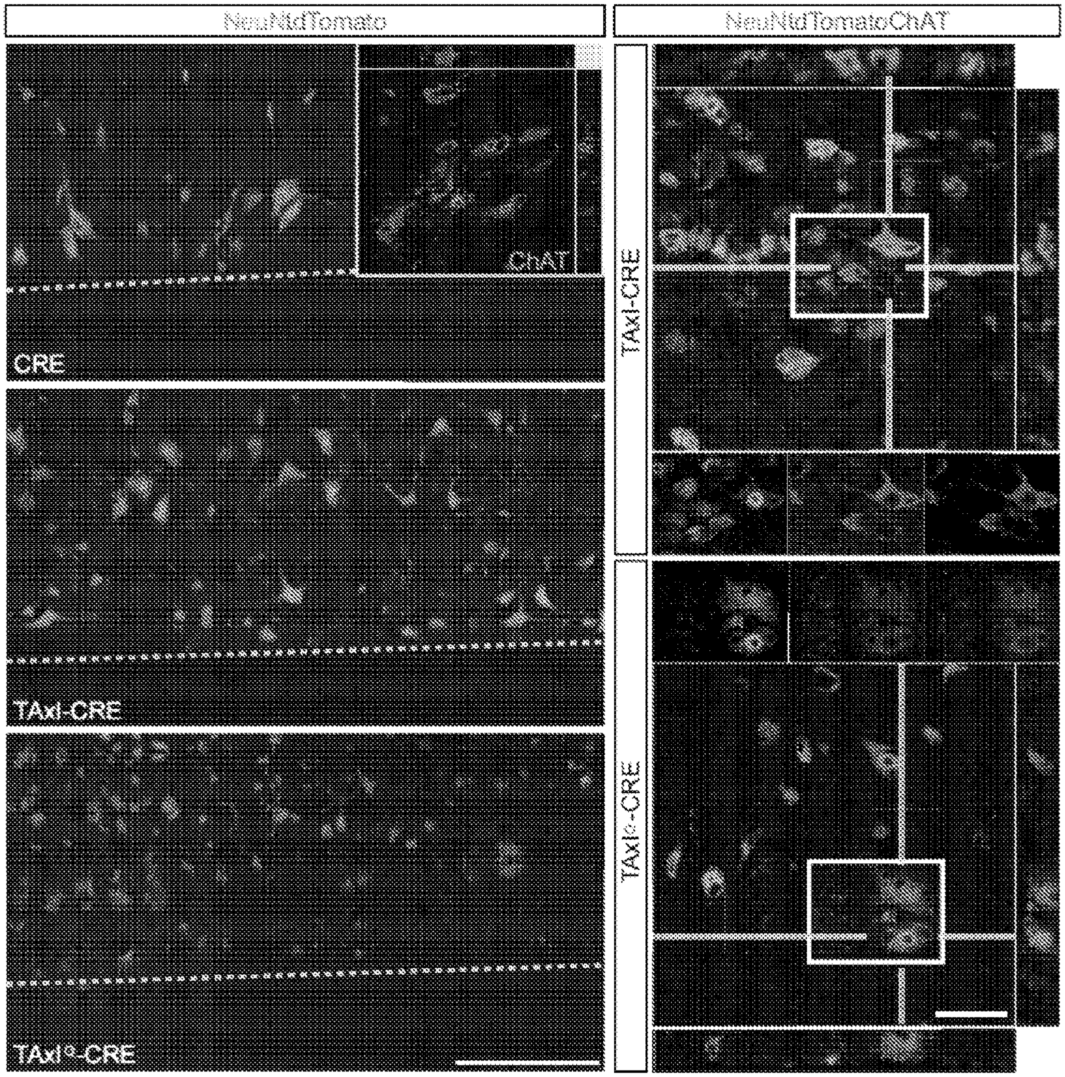
FIG. 5. Photomicrographs showing that TAxI delivers Cre into spinal cord motor neurons after IM injection. Recombinant Cre proteins (Cre, TAxI-Cre, and TAxI$^Q$-Cre) were injected (2.5 μg) into the gastrocnemius of Ai14 reporter mice. Delivery of Cre recombinase into cells was confirmed by reporter-protein expression (tdTomato) in neurons stained by immunofluorescence for neuronal nuclear marker (NeuN) in the grey matter (above the dotted line. Bar, 50 μm.) of the lumbar spinal cord. Orthogonal z-planes from confocal micrographs show td-Tomato expression in NeuN-labeled cells that express ChAT. Insets show individual channels for NeuN, ChAT, and tdTomato in representative motor neurons from TAxI-Cre and TAxI$^Q$-Cre injected animals. Bar, 10 μm.

To have utility as a therapeutic protein delivery system, the TAxI peptide must traffic cargo without rapid degradation or sequestration. To test for TAxI-mediated delivery of active enzyme to the spinal cord, we generated a series of Cre recombinase chimeras: wild-type Cre (Cre), Cre fused to the TAxI peptide (TAxI-Cre), and Cre fused to a mutated TAxI moiety ($TAxI^Q$-Cre). After purification, each recombinant Cre protein was injected (2.5 μg) into the gastrocnemius of the Ai14 reporter mice. In these mice, delivery of biologically active Cre recombinase results in td-Tomato expression due the excision of a floxed stop-codon.[27] One week post-injection, confocal microscopy was used to image spinal cords isolated after perfusion fixation. Animals injected with Cre possessed small punctuate tdTomato$^{+}$-cells that resembled blood-monocytes dispersed throughout the lumbar spinal cord and around vascular elements (FIG. 5). In contrast, the lumbar spinal cord of TAxI-Cre injected animals contained many tdTomato$^{+}$-cells that had the complex morphology and large-bore dendritic processes, hallmark characteristics of motor neurons, (FIG. 5) throughout the grey matter. Furthermore, td-Tomato$^{+}$-cells projected into intermediate lamina of the spinal cord as well as into interneuron polls within multiple longitudinal segments, similar to efferent motor neurons (inset). The cells also displayed prominent nucleoli and bulbous cell bodies, to further support the morphological identification of mature neurons. In contrast, TAxI$^{\mathcal{Q}}$-Cre injected animals showed limited tdTomato express in isolated regions of the gray matter, adjacent to the white matter only (FIG. 5, dotted lined delimits the gray-to-white matter boundary). Spinal cords stained with NeuN antibodies and ChAT showed tdTomato colocalized with these markers in cells within the spinal cord of TAxI- and TAxI$^{\mathcal{Q}}$-Cre injected animals, confirming reporter expression within spinal motor neurons (FIG. 5). In contrast to the NeutrAvidin complexes, TAxI$^{\mathcal{Q}}$-Cre showed a limited ability to deliver Cre in to the spinal cord. However, the efficiency and number of cells transduced by TAxI$^{\mathcal{Q}}$-Cre was significantly reduced compared to TAxI-Cre, which suggests that the TAxI$^{\mathcal{Q}}$ mutations reduced its affinity for its target but was not able to eliminate uptake. In contrast wt-Cre did not induce tdTomato expression in either NeuN or ChAT-positive cells.

Fusion proteins bearing the HIV TAT protein have been shown previously to cross cell membranes[28, 29]. However, these cell-penetrating peptides have not been shown to transduce the CNS neurons in vivo. This result was therefore further confirmed using an alternate mT/mG reporter mouse strain and using TAT-Cre for comparison. TAxI-mediated Cre recombinase delivery to the CNS was more efficient in mice injected with TAxI-Cre versus mice injected with TAT-Cre. Thus, recombinant TAxI-Cre possessed the unique capability to import active protein and to facilitate recombination in the nucleus of spinal cord neurons.

This work presents several notable advances. First, in vivo library screening was successfully used to identify a peptide sequence with the ability to mediate transport into the CNS after an injection into peripheral muscle. While the majority of in vivo phage screens have selected for binding to organ-prevalent endothelial targets,[30, 31] or attempted to screen for a brain-homing peptide after nasal application,[32] the studies presented here show significant and efficient delivery of phage into the spinal cord. Furthermore, the synthetic peptide derived from the phage sequence showed efficient sequence-specific transport to the CNS.

Second, biologically active protein chimeras comprised of the TAxI moiety fused to Cre recombinase are delivered to the spinal cord. Proteins such as glial cell line-derived neurotrophic factor (GDNF), insulin-like growth factor (IGF) and superoxide dismutase (SOD) have been fused with the tetanus toxin fragment C and shown to be successfully transported to the spinal cord from peripheral injections.[17, 20, 33] However in all these examples, no therapeutic effect or biological activity could be shown from the delivered proteins.[33] In contrast, Cre delivery via an TAxI moiety resulted in significant gene recombination in spinal cord neurons (FIG. 5). While Cre has been delivered in vivo by viral gene delivery using adenovirus, lentivirus, and adeno-associated virus [34-36], the TAxI-Cre we describe herein is the first non-viral delivery paradigm to transduce a biologically active Cre in vivo. Cell penetrating peptides such as TAT have been used to deliver recombinant Cre in cultured cells or explants cultures.[28, 35, 37] Still, efficient TAT-mediated delivery of Cre requires conjugation to nuclear localization peptides to enhance its natural energy-dependent nuclear transport mechanism and membrane destabilizing peptides to facilitate intracellular vesicular release.[37-39] The TAxI peptide delivered wild-type Cre more efficiently and specifically to neurons in the CNS compared to the TAT-Cre construct that was used here as a positive control.

Finally, our data suggests that the TAxI peptide is able to target the transport of cargos through non-degrading pathways within somatic motor neurons. We demonstrate that TAxI-Cre was able to mediate import of a biologically active protein (i.e. Cre recombinase) to elicit transgene expression in motor neurons (FIG. 5). Similarly, TAxI-phage were recovered from the spinal cord 24 hours after delivery, as opposed studies that have shown that M13 phage modified with asialoglycoprotein or scavenger receptors ligands undergo rapid degradation (up to 5000-fold) after internalization.[24] Furthermore, the data presented here suggests that TAxI-Cre has a high propensity for targeting somatic motor neurons via intramuscular injection. Thus, the TAxI peptide could be used to deliver proteins or other biologics and therapeutics to treat a variety of motor neuron diseases (such as ALS) or to deliver regenerative approaches in the case of nerve injury. The TAxI peptide possesses tremendous therapeutic potential for targets in the CNS.

Materials and Methods

Animals.

The Institutional Animal Care and Use Committee (IACUC) at the University of Washington authorized all animal work in accordance with animal use and regulations. C57bl/6 and B6; 129S6-Gt(ROSA)26Sortm14(CAG-tdTomato)Hze/J mice and Gt(ROSA)26Sortm4(ACTB-tdTomato, -EGFP)Luo/J were purchased from The Jackson Laboratory.

Intramuscular Phage Delivery and Library Screening.

For library screening, a 50:50 mixture of a linear and circularized bacteriophage libraries (Ph. D.-12 and C7C phage library, New England Biolabs, USA), $1.5\times10^{13}$ pfu/mL in 5% glucose, was injected bilaterally into the gastrocnemius muscle of C57bl/6 mice (5 μl each side). Spinal cord and cardiac tissue was harvested after transcardiac perfusion with 20 mL saline at 8, 24, and 48 hours post-injection and flash-frozen with liquid-nitrogen. Tissue homogenates in DMEM (Invitrogen, Inc.) with 1% BSA (Fisher Scientific) were centrifuged and resuspended in 1% Triton-X 100 (Sigma-Aldrich, Inc.) and further homogenized by passage through a 25-gauge needle. The phage titer was determined following standard protocol and an aliquot of the remaining tissue homogenate was amplified and concentrated by precipitation in a polyethyleneglycol (PEG) and sodium chloride solution (Sigma-Aldrich, Inc.). After amplification, the second round stock was titered on X-gal LB-agar plates, and resuspended in 5% glucose ($1.0\times10^{13}$ pfu/mL) and a subsequent round of phage injection and tissue harvest was performed (as necessary). For phage delivery of purified phage clones, $1\times10^{9}$ pfu/mL of phage were injected as described above.

Immunohistochemistry.

After treatment and transcardiac perfusion, tissues were equilibrated in 30% sucrose for cyroprotection and embedded in OTC for serially sectioning (1:6, 20 μm coronal/cross-sections) with a Leica SM1850 cryostat. Primary antibodies previously shown to identify reactive astrocytes (glial fibrillary acidic protein, GFAP), neurons (microtubule associated protein 2, Map2; Sigma and neuron nuclear antigen, NeuN; Chemicon) were used to elucidate cell phenotype. Excessive rinses in 0.1 M TBS pH 7.5 and once in blocking buffer (supplemented with α-mouse IgG, where needed) removed unbound primary antibodies, and secondary antibodies were applied in blocking buffer for 2 hours at room temperature, or overnight at 4° C.: donkey α-mouse IgG conjugates and α-rabbit IgG conjugates (1:500, Jackson Labs). Unbound antibody was removed by extensive washes with blocking buffer. Sections were imaged by confocal microscopy with a Nikon TS2000E equipped with a krypton/argon laser, a red diode laser, and an infinity corrected 40×1.4 NA lens. Volocity (Improvision Software) managed each digital images and reconstructed z-series stacks. Final image presentation was produced with Photoshop (Adobe Software). Cells populations in the spinal cord were calculated via fractionator stereology and Stereo Investigator (Microbrightfield, Inc.).

Primary Neuron Isolation and Cell Binding Studies.

Collagenase IV (900 U/mL, Worthington Inc.), DNase (1000 U/mL, Worthington Inc.), Papain (3 U/mL, Worthington Inc.) in L-15 media (Invitrogen) supplemented with antibiotics (Penn/Strep, Gibco) was used to dissociate the cerebullum, which was extracted from exsanguinated (saline perfusion) neonatal mice (P6-P7). Tissue chunks were triturated to aide dissociation (10 minute intervals) with constant shaking at 37° C. for 30 min. The cell slurry was passed through a 100 μm cell strainer (Falcon) to remove fat and tissue debris, and excess enzyme was removed by three successive rinses in ice-cold L-15 and centrifugation (3 minutes, 1000 g). After the final rinse, the pellet was resuspended in L-15 media (minimal volume) and layered on top of 10% Percoll gradient (Pharmigen). Neurons were enriched and separated from blood cells and other CNS matter by centrifugation (400×·g, Beckman Inc.) Excess percoll was removed by successive rinses in L-15. Neuronal cells were resuspend in Neurobasal media supplemented with 1% N2 (Gibco-Invitrogen) and 2% B27 (Gibco-Invitrogen), counted and plated on glass coverslips coated with 50:50 mix poly-L-lysine (0.01%, Sigma) and laminin (10 μg/mL, BD Bioscience) for 5-7 days. Growth media was supplemented with 1% BSA as a block, and incubated 30 minutes at 3° C. Daylight Streptavidin-488 (Pierce) was mixed with a biotinylated peptide (molar ratio 1:1) and allowed to incubate 30 minutes prior to use. Streptavidin:peptide complexes (1 μM in neurobasal growth media with 1% BSA) was incubated with cells for 30 minutes at 37° C. HBSS+1% BSA was used to rinse the cells 3 times (15 minutes each). After incubation in CellScrub buffer (Genlantis, USA), an additional rinse was applied and then the cells were fixed with 4% paraformaldehyde. Immunofluorescence was used to counterstain neurons (Map2) and nuclei via DAPI stain with imaging by confocal microscopy. After optimization, a standard laser setting was used to capture images at sites selected randomly. After capture, ImageJ was used to quantify the fluorescence intensity (integrated density) on the raw images for each coverslip.

Peptide Synthesis.

Biotinylated peptides were synthesized by standard FMOC solid phase peptide synthesis and NHS-biotin (Pierce Chemicals) was conjugated to the amine terminus in DMF before trifluoroacetic acid deprotection and cleavage from the resin. Peptides were purified by HPLC to >90% purity. Desired peptides were confirmed by MALDI mass spectrometry analysis. Three peptides were synthesized: TAxI: SACQSQSQMRCGGG (SEQ ID NO: 8), TAxI$^{L}$: SAAQSQSQMRAGGG (SEQ ID NO: 20), TAxI$^{Q}$: GGCASGAQARCGG (SEQ ID NO: 9).

Tissue Harvests for Biodistribution and Avidin ELISA.

After IM injection of isolated phage clones and NeutrAvidin:peptide complexes, the organs of exsanguinated mice were isolated and snap-frozen with liquid nitrogen. Prior to homogenization, tissues were rinsed with tris-buffered saline and homogenized in tissue buffer (Sigma). After centrifugation to remove debris, the protein concentration of each tissue lysate was determined by BCA assay. Bacteriophage biodistribution was titered by infection of ER2738 *e. coli* and plaque counts on X-gal LB agar plates. Each tissue was plated in triplicate.

To determine the biodistribution of NeutrAvidin:peptide complexes, a sandwich ELISA was used. A monoclonal mouse anti-avidin antibody (Pierce) was used as the capture antibody, and was used to coat the well of a 96-well plate. After coating, each well was blocked (TBS, +1.0% BSA, +0.5% Tween-20) for 30 minutes at room temperature. After block, each well was loaded with 5 μg (protein concentration) of each tissue homogenate (in triplicate) and incubated one hour at room temperature. Subsequently, each was washed three times with TBS+0.1% Tween-20 (TBS-T) and then incubated with a rabbit anti-avidin antibody (Sigma). A donkey anti-rabbit horseradish peroxidase (HRP) conjugate was used to detect the rabbit antibody and the amount of bound antibody was quantified by luminescence (ECL HRP substrate) and quantified on a Envision luminometer (Perkin-Elmer).

Recombinant Cre Expression and Purification.

The coding sequence for Cre recombinase was obtained from the University of Washington Yeast Resource Center. The TAxI peptide sequence was added to the 5-prime end and both TAxI-Cre and wild-type Cre were subcloned into pRSETb (Invitrogen). To allow for expression and purifaction, each plasmid was transformed into BL21(D3)pLysS and grown in media supplemented with IPTG/X-gal (Promega). After centrifugation, B-PER (Pierce, Thermo Scientific) was used to lyse the bacterial cultures and each recombinant 6×-his-tagged protein was purified on a Ni-NTA column (Standard manufacturer protocol: Pierce, Thermo Sci.). After elution, each peptide solution was concentrated in millipore centricon and the final buffer was exchanged by on a PD10 column or centricon (20 mM $PO_4$ pH 7.5; 0.5M NaCl; 5% glycerol) prior to injection into ROSA reporter mice.

Microscopy.

Confocal images were acquired on a Nikon A1R confocal mounted on a Nikon TiE inverted microscope with a 40×1.4 NA objective lens. Multiphoton excitation microscopic images were captured using an Olympus FV1000MPE multiphoton microscope equipped with a 25× SuperObjective (Olympus) and Mai Tai laser (Spectra Physics). Images were processed using Improvision Volocity (3.0.2), IMaris and Adobe Photoshop CS4 (11.01).

Statistical Analysis.

A non-paired students t-test evaluated differences in phage and avidin biodistribution, as well as the differences in streptavidin:peptide complexes in vitro. For all statistical analyses, significance was accepted at a p value of 0.05 and lower.

REFERENCES

1. Barchet, T. M. and M. M. Amiji, Expert Opinion on Drug Delivery, 2009. 6(3): p. 211-225.
2. Begley, D. J., Pharmacology & Therapeutics, 2004. 104(1): p. 29-45.
3. Thorne, R. G. and W. H. Frey, 2nd, Clin Pharmacokinet, 2001. 40(12): p. 907-46.
4. Windebank, A. J., Adv Neurol, 1995. 68: p. 229-34.
5. Spencer, B. J. and I. M. Verma, Proceedings of the National Academy of Sciences of the United States of America, 2007. 104(18): p. 7594-7599.

6. Kumar, P., et al., Nature, 2007. 448(7149): p. 39-43.
7. Yu, Y. J., et al., Science Translational Medicine, 2011. 3(84).
8. Mitchell, J. D. and G. D. Borasio, Lancet, 2007. 369(9578): p. 2031-2041.
9. Monani, U. R., Neuron, 2005. 48(6): p. 885-896.
10. Federici, T. and N. M. Boulis, Muscle & Nerve, 2006. 33(3): p. 302-323.
11. Azzouz, M., et al., Nature, 2004. 429(6990): p. 413-417.
12. Boulis, N. M., et al., Neurosurgery, 1999. 45(1): p. 131-137.
13. Foust, K. D., et al., Nature Biotechnology, 2010. 28(3): p. 271-U126.
14. Glorioso, J. C. and D. J. Fink, Molecular Therapy, 2009. 17(1): p. 13-18.
15. Kaspar, B. K., et al., Science, 2003. 301(5634): p. 839-842.
16. Carlton, E., et al., Neurosurgery, 2008. 63(6): p. 1175-1182.
17. Chian, R. J., et al., Brain Research, 2009. 1287: p. 1-19.
18. Federici, T., et al., Neurosurgery, 2007. 60(5): p. 911-918.
19. Figueiredo, D. M., et al., Experimental Neurology, 1997. 145(2): p. 546-554.
20. L1, J. H., et al., Biochemical and Biophysical Research Communications, 2009. 390(3): p. 947-951.
21. Francis, J. W., et al., Brain Res, 2004. 995(1): p. 84-96.
22. Perez, M. C. P., et al., Gene Therapy, 2004. 11(13): p. 1023-1032.
23. Zou, J., et al., Molecular Biology Reports, 2004. 31(2): p. 121-129.
24. Molenaar, T. J. M., et al., Virology, 2002. 293(1): p. 182-191.
25. Jacquin, M. F. and R. W. Rhoades, Somatosens Mot Res, 1990. 7(3): p. 265-88.
26. Rigaud, M., et al., Pain, 2008. 136(1-2): p. 188-201.
27. Madisen, L., et al., Nat Neurosci. 13(1): p. 133-40.
28. Gitton, Y., et al., Bmc Biotechnology, 2009. 9.
29. Nagahara, H., et al., Nat Med, 1998. 4(12): p. 1449-52.
30. L1, J. W., et al., Biomaterials, 2011. 32(21): p. 4943-4950.
31. Pasqualini, R., E. Koivunen, and E. Ruoslahti, Nature Biotechnology, 1997. 15(6): p. 542-546.
32. Wan, X. M., et al., Peptides, 2009. 30(2): p. 343-350.
33. Figueiredo, D. M., et al., Journal of Natural Toxins, 2000. 9(4): p. 363-379.
34. Kaspar, B. K., et al., Proceedings of the National Academy of Sciences of the United States of America, 2002. 99(4): p. 2320-2325.
35. Pfeifer, A., et al., Proceedings of the National Academy of Sciences of the United States of America, 2001. 98(20): p. 11450-11455.
36. Wang, Y., L. A. Krushel, and G. M. Edelman, Proceedings of the National Academy of Sciences of the United States of America, 1996. 93(9): p. 3932-3936.
37. Wadia, J. S., R. V. Stan, and S. F. Dowdy, Nature Medicine, 2004. 10(3): p. 310-315.
38. Peitz, M., et al., Proceedings of the National Academy of Sciences of the United States of America, 2002. 99(7): p. 4489-4494.
39. Le, Y. Z., et al., Nucleic Acids Research, 1999. 27(24): p. 4703-4709.

Example 2

Identification of Additional Transport Peptides Capable of Delivery to CNS

The methods described above in Example 1 also led to the discovery of additional transport peptides. The following peptides were successfully transported to CNS sites after injection into gastrocnemius:

| Clone/Name | Amino Acid Sequence | With Flanking Sequence | SEQ ID NO: |
|---|---|---|---|
| 8a | PF | **SAC**PF**CGGG** | 3*; 10 |
| 0808 | LQATPSA | **SAC**LQATPSA**CGGG** | 4; 11 |
| 2407 | ISPSLSS | **SAC**ISPSLSS**CGGG** | 5: 12 |
| 4802 | TSTGFRG | **SAC**TSTGFRG**CGGG** | 6; 13 |
| 4042 | TSTAPHLRLRLTSR | (none) | 7 |

*SEQ ID NO: 3 is CPFC, which shows the two amino acid 8a peptide PF flanked by cysteines, illustrating one optional form of this peptide.

Example 3

Additional Methods of Peripheral Administration of Transport Peptide

The methods described above in Example 1 were modified to explore alternative modes of delivery to intramuscular injection. Intraperitoneal injection was attempted using peptides 2404, 2404Q, and 4042, and proved successful, resulting in robust delivery to the CNS.

Example 4

Peptide-2404 Labels Ventral Motor Neurons in Human Spinal Cord

Figures 6A, 6B, 6C, 6D:
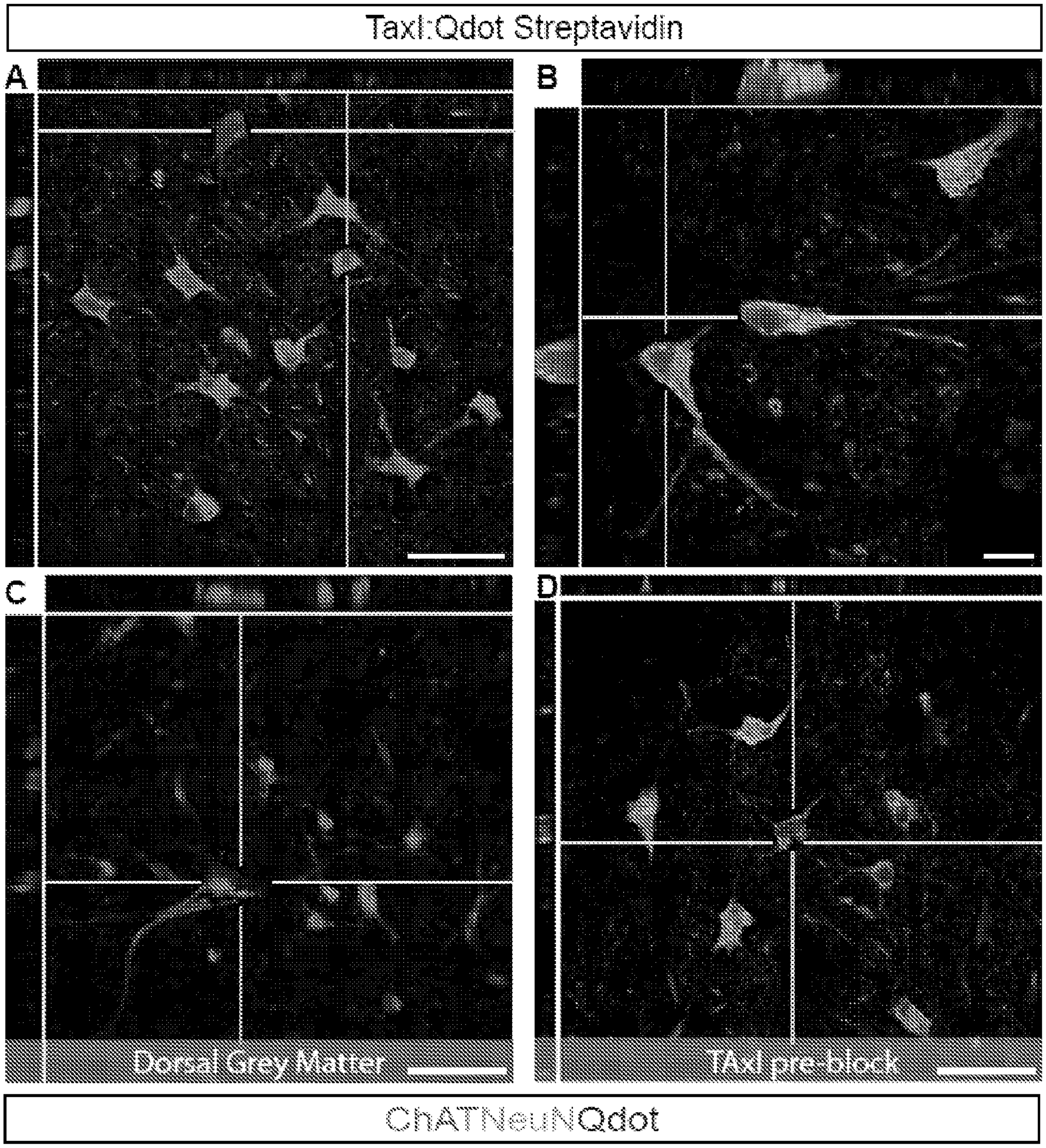
FIGS. 6A-6D. Photomicrographs showing TAxI-Streptavidin labels neurons in the adult human spinal cord. Steptavidin conjugated quantum dots (Qdots) were complexed with biotinylated TAxI peptide and incubated on human spinal cord tissue with anti-NeuN and anti-ChAT antibodies.

The ability to target motor neurons that transport peptide-protein complexes and biologically active proteins into the spinal cord provides tremendous potential for utilizing and delivering novel therapeutics for the CNS. This Example examined whether the 2404-peptide could bind to neural elements within the fresh frozen sections of the human spinal cord. Indeed, biotinylate-2404 complexed with quantum dot conjugated streptavidin colocalized with NeuN and ChAT in ventral-horn motor neurons (FIG. 6A). High-resolution confocal micrographs showed the 2404-streptavidin complexes labeled the nuclei of NeuN+-neurons (FIG. 6B). 2404-steptavidin labeled cells were not prominent in dorsal aspects of the spinal cord. However, 2404-streptavidin labeled interneurons could be seen in the dorsal grey matter (FIG. 6C), and tissue pre-blocked with 10× excess 2404-peptide showed a significant reduction in motor neurons labeled by 2404-streptavidin (FIG. 6D). Together, these results indicate that 2404-peptide is able to bind and label neurons in the human spinal cord specifically, and confirm the ability of the 2404-peptide to deliver therapeutics into the human CNS.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A recombinant or synthetic transport peptide, or polynucleotide encoding same, or a derivative thereof having at least one amino acid or nucleic acid substituted with a non-natural derivative of the indicated amino acid or nucleic acid, wherein the peptide comprises the amino acid sequence QSQSQMR (SEQ ID NO: 1), or TSTAPHLRLRLTSR (SEQ ID NO: 7), and wherein the transport peptide further comprises a heterologous molecule attached thereto by chemical conjugation or expression as a fusion partner.

2. The transport peptide of claim 1, wherein the heterologous molecule is a polypeptide, antibody, polynucleotide, vector, delivery vehicle, small molecule or drug.

3. The transport peptide of claim 1, wherein the polypeptide is an enzyme or a growth factor.

4. The transport peptide of claim 1, wherein the polynucleotide is a siRNA molecule.

5. The transport peptide of claim 1, which is a fusion protein comprising the transport peptide fused with a heterologous peptide.

6. The fusion protein of claim 5, wherein the heterologous peptide is selected from the group consisting of enzymes, growth factors, antibodies, and therapeutic peptides.

7. The transport peptide of claim 1, wherein the peptide comprises the amino acid sequence of SEQ ID NO: 1.

8. The transport peptide of claim 1, further comprising a flanking sequence that mediates incorporation into a carrier.

9. The transport peptide of claim 1, wherein the peptide comprises the amino acid sequence of SEQ ID NO: 8.

10. The transport peptide of claim 1, wherein the non-natural derivative is a D-amino acid, β-amino acid, or a chemically modified amino acid.

11. The transport peptide of claim 1, wherein the peptide exhibits at least 90% identity with SEQ ID NO: 7 or 8.

12. The transport peptide of claim 1, wherein the peptide is fewer than 50 amino acids in length.

13. The transport peptide of claim 1, wherein the peptide is 10-20 amino acids in length.

14. A method of delivering a molecule to a central nervous system (CNS) site of a subject, the method comprising administering the transport peptide of claim 1 to a peripheral site of the subject.

15. The method of claim 14, wherein the administering comprises intramuscular administration, intraperitoneal administration, intranasal administration, intravenous administration or subcutaneous administration.

16. The method of claim 14, wherein the CNS site is the spinal cord.

17. The method of claim 14, wherein the molecule delivered is a therapeutic agent.

18. The method of claim 17, wherein the therapeutic agent is a small molecule, polypeptide, antibody, polynucleotide, or drug.

19. A method of treating a CNS condition in a subject, the method comprising administering to a peripheral site of the subject the transport peptide of claim 1, wherein the heterologous molecule is a therapeutic agent.

20. The method of claim 19, wherein the CNS condition is a neurodegenerative disease, stroke or chronic pain.

* * * * *